(12) United States Patent
Newton et al.

(10) Patent No.: US 7,422,589 B2
(45) Date of Patent: Sep. 9, 2008

(54) SYSTEM AND METHOD FOR PERFORMING AN ELECTROSURGICAL PROCEDURE

(75) Inventors: David W. Newton, Longmont, CO (US); Roger C. Odell, Louisville, CO (US)

(73) Assignee: Encision, Inc., Boulder, CO (US)

( * ) Notice: Subject to any disclaimer, the term of this patent is extended or adjusted under 35 U.S.C. 154(b) by 0 days.

(21) Appl. No.: 11/202,915

(22) Filed: Aug. 12, 2005

(65) Prior Publication Data
US 2006/0041253 A1 Feb. 23, 2006

Related U.S. Application Data

(60) Provisional application No. 60/602,103, filed on Aug. 17, 2004.

(51) Int. Cl.
*A61B 18/18* (2006.01)
(52) U.S. Cl. .............................. 606/46; 606/35; 606/32
(58) Field of Classification Search ............. 606/32–35, 606/45–47; 600/104
See application file for complete search history.

(56) References Cited

U.S. PATENT DOCUMENTS

| | | | |
|---|---|---|---|
| 1,754,806 A | 4/1930 | Stevenson |
| 2,004,559 A | 6/1935 | Wappler |
| 2,008,367 A | 7/1935 | Rhinevault |
| 2,448,741 A | 9/1948 | Scott |
| 2,741,248 A | 11/1956 | Woodhall |
| 3,070,132 A | 4/1962 | Sheridan |
| 3,580,983 A | 5/1971 | Jackson |
| 3,585,985 A | 6/1971 | Gould |
| 3,601,126 A | 8/1971 | Estes |
| 3,706,008 A | 12/1972 | Kremer |
| 3,707,149 A | 12/1972 | Hao |
| 3,804,096 A | 4/1974 | Gonser |
| 3,834,392 A | 9/1974 | Lampman |

(Continued)

FOREIGN PATENT DOCUMENTS

DE 1139927 8/1961

(Continued)

OTHER PUBLICATIONS

PCT/US/029016; Notification of Transmittal of the International Search Report and Written Opinion of the International Searching Authority or the Declaration mailed Apr. 12, 2006.

(Continued)

*Primary Examiner*—Michael Peffley
(74) *Attorney, Agent, or Firm*—Neugeboren O'Dowd PC; Sean R. O'Dowd

(57) ABSTRACT

A system and method for performing an electrosurgical procedure are disclosed. The method includes obtaining information indicative of at least one physical characteristic of the patient and generating a reference voltage that is derived, at least in part, from the information. The reference voltage is coupled to a body of the electrosurgical apparatus, and the reference voltage is generated to a level so as to limit any difference between a voltage of the patient and a voltage of the body of the electrosurgical apparatus. In variations, the reference voltage is varied on an ongoing basis so as to adapt the reference voltage to one or more changing physical characteristics of the patient.

16 Claims, 15 Drawing Sheets

U.S. PATENT DOCUMENTS

| | | |
|---|---|---|
| 3,838,242 A | 9/1974 | Goucher |
| 3,895,635 A | 7/1975 | Justus |
| 3,898,991 A | 8/1975 | Ikuno |
| 3,905,373 A | 9/1975 | Gonser |
| 3,913,583 A | 10/1975 | Bross |
| 3,933,157 A | 1/1976 | Bjurwill |
| 3,946,738 A | 3/1976 | Newton |
| 3,963,856 A | 6/1976 | Carlson |
| 3,994,287 A | 11/1976 | Turp |
| 4,003,380 A | 1/1977 | Wien |
| 4,084,594 A | 4/1978 | Mosior |
| 4,181,131 A | 1/1980 | Ogiu |
| 4,184,492 A * | 1/1980 | Meinke et al. ............... 606/35 |
| 4,200,104 A | 4/1980 | Harris |
| 4,231,372 A | 11/1980 | Newton |
| 4,237,887 A | 12/1980 | Gonser |
| 4,248,716 A | 2/1981 | LaValley |
| 4,303,073 A | 12/1981 | Archibald |
| 4,311,144 A | 1/1982 | Harada |
| 4,325,374 A | 4/1982 | Komiya |
| 4,343,308 A | 8/1982 | Gross |
| 4,367,746 A | 1/1983 | Derechinsky |
| 4,374,517 A * | 2/1983 | Hagiwara ................. 600/104 |
| 4,433,687 A | 2/1984 | Burke |
| 4,440,170 A | 4/1984 | Golden |
| 4,449,532 A | 5/1984 | Story |
| 4,494,541 A | 1/1985 | Archibald |
| 4,601,710 A | 7/1986 | Moll |
| 4,615,330 A | 10/1986 | Nagasaki |
| 4,617,927 A | 10/1986 | Manes |
| 4,618,885 A | 10/1986 | Nagasaki |
| 4,638,802 A | 1/1987 | Okada |
| 4,657,015 A | 4/1987 | Irnich et al. |
| 4,662,369 A | 5/1987 | Ensslin |
| 4,674,501 A | 6/1987 | Greenberg |
| 4,716,897 A | 1/1988 | Noguchi |
| 4,741,334 A | 5/1988 | Irnich |
| 4,744,361 A | 5/1988 | Karaswa |
| 4,844,063 A | 7/1989 | Clark |
| 4,886,505 A | 12/1989 | Haynes |
| 4,919,129 A | 4/1990 | Weber |
| 4,983,456 A | 1/1991 | Iwaskow |
| 5,007,257 A | 4/1991 | Farrin |
| 5,009,643 A | 4/1991 | Reich |
| 5,087,257 A | 2/1992 | Farin |
| 5,116,353 A | 5/1992 | Green |
| 5,147,357 A | 9/1992 | Rose |
| 5,176,702 A | 1/1993 | Bales |
| 5,263,967 A | 11/1993 | Lyons |
| 5,275,615 A | 1/1994 | Rose |
| 5,277,696 A | 1/1994 | Hagen |
| 5,295,993 A | 3/1994 | Green |
| 5,308,358 A | 5/1994 | Bond |
| 5,312,401 A | 5/1994 | Newton |
| 5,334,198 A | 8/1994 | Hart |
| 5,344,428 A | 9/1994 | Griffiths |
| 5,431,638 A | 7/1995 | Hennig |
| 5,432,459 A | 7/1995 | Thompson et al. |
| 5,436,566 A | 7/1995 | Thompson et al. |
| 5,571,137 A | 11/1996 | Marlow |
| 5,688,269 A * | 11/1997 | Newton et al. ............... 606/46 |
| 5,752,951 A | 5/1998 | Yanik et al. |
| 5,769,841 A | 6/1998 | Odell et al. |
| 5,792,141 A * | 8/1998 | Logeman ................... 606/46 |
| 5,919,191 A | 7/1999 | Lennox |
| 6,039,732 A | 3/2000 | Ichikawa et al. |
| 6,113,597 A | 9/2000 | Eggers |
| 6,245,063 B1 | 6/2001 | Uphoff |
| 6,277,114 B1 | 8/2001 | Bullivant |
| 6,471,701 B2 | 10/2002 | Brommersma |
| 6,634,924 B1 | 10/2003 | Ono |
| 6,929,643 B2 | 8/2005 | Ohyama |
| 2004/0019351 A1 | 1/2004 | Ohyama |
| 2004/0167515 A1 | 8/2004 | Peterson et al. |
| 2005/0251134 A1 | 11/2005 | Woloszko |

FOREIGN PATENT DOCUMENTS

| | | |
|---|---|---|
| DE | 3013784 | 10/1980 |
| DE | 44-19-070 A1 | 12/1994 |
| JP | 53-13583 | 2/1978 |

OTHER PUBLICATIONS

International Preliminary Report on Patentability Mailed Mar. 1, 2007.

Examiner John Dicicco, Advisory Action: Related U.S. Appl. No. 11/202,605, filed Oct. 25, 2007, United States Patent Office.

Odel et al, Election and Amendment of Related Related U.S. Appl. No. 11/202,605, filed Feb. 24, 2007, United States Patent Office.

Examiner Jacqueline Papapietro, Office Action: Related U.S. Appl. No. 11/202,458, filed Aug. 17, 2007, United States Patent Office.

Odel et al, Response to Office Action of Related Related U.S. Appl. No. 11/202,458, filed Jan. 17, 2008, United States Patent Office.

* cited by examiner

Electrode Assembly

Section J-J

SYSTEM AND METHOD FOR PERFORMING AN ELECTROSURGICAL PROCEDURE

PRIORITY

The present application claims priority from commonly owned and assigned provisional application No. 60/602,103, entitled SYSTEM FOR MONITORING RESECTOSCOPES AND RELATED ELECTROSURGICAL INSTRUMENTS, filed Aug. 17, 2004, which is incorporated herein by reference.

RELATED APPLICATIONS

The present application is related to the following commonly owned and assigned application: Application No. (11/202,605), entitled SYSTEM AND METHOD FOR MONITORING ELECTROSURGICAL INSTRUMENTS, filed herewith; and Application No. (11/202,458), entitled ELECTROSURGICAL SYSTEM AND METHOD, filed herewith, each of which is incorporated herein by reference.

FIELD OF THE INVENTION

The present invention relates to surgical techniques and devices. In particular, but not by way of limitation, the present invention relates to electrosurgical techniques.

BACKGROUND OF THE INVENTION

The problems arising with the use of electrosurgical instruments where the field of view of the surgeon is limited are well-known. Traditional laparoscopic electrosurgical tools include a trocar sheath or other cannula that is inserted into a patient's body and that provides a conduit for a surgeon to introduce various surgical cutting tools, optics for increased visualization, irrigation, active surgical electrodes, and other devices to be used during a surgical procedure.

One problem arises if the insulation on the active electrode is damaged thereby allowing the active current (possibly in the form of arcing) to pass there-through directly to the patient's tissue whereby unintended and potentially unknown injury, possibly in the form of a life threatening infection, can occur. The arcing may occur out of the surgeon's field of view which may extend as little as about 2 centimeters from the tip of the active electrode (or the surgical field). The field of view is typically established by illumination and viewing sources. In the context of prior art laparoscopic instruments, the illumination and/or viewing sources are established through one or more other trocar sheaths at other incisions.

Particularly with electrosurgical instruments, there can be many centimeters of the active electrode which extend between the entry point in a patient's body and the surgeon's field of view, typically at the distal end of the active electrode and near the point where electrosurgery takes place. The area of the electrosurgical instrument, and in particular the active electrode, that is out of the field of view of the surgeon is potentially dangerous if left in an unmonitored state. In this situation, the insulated active electrode may unintentionally come into contact with unknown tissue of the patient may cause serious injury that might not be noticed by the surgeon during the procedure.

If arcing resulting from the damaged insulation were to occur within the field of view of the surgeon, the surgeon would normally observe this and immediately deactivate the generator. Arcing, however, is prone to occur at a site remote from the field of view of the surgeon, and as a consequence, damage to the active electrode insulation is particularly a problem because it may go undetected while the full active current passes through an unintended path of the patient's tissue from the active electrode to the return electrode.

A second problem that can arise is caused by a capacitive effect where one electrode of the capacitance is the active electrode and the other electrode of the capacitance is the metallic trocar sheath. The dielectric between these elements is the insulation on the active electrode. Current from the active electrode will be capacitively coupled to the trocar sheath and then returned through the body and the return electrode to the generator. If this current becomes concentrated, for example, between the trocar sheath and an organ such as the bowel, the capacitive current can cause a burn to the organ.

With respect to the use of laparoscopic electrosurgical tools, the above problems have been preliminary addressed by the use of a safety shield and/or monitoring circuitry which serves to deactivate the electrosurgical generator and accompanying current flow if an abnormal condition occurs. For example, U.S. Pat. Nos. 5,312,401, 5,688,269, 5,769,841 and 6,494,877, assigned to Encision, Inc., describe solutions to these problems. All of the details of these patents are hereby incorporated into the present application by reference in their entirety.

U.S. Pat. No. 4,184,492, by Meinke, discloses, in general, a system in which a resecting apparatus includes a connection between an outer tube (metallic) and a lead means (the return electrode) with an impedance of 100-1000 ohms. The purpose is to minimize or avoid burns to the patient and user touching the metallic parts of the instrument. There may be a monitor included in the connections to display unsafe conditions and also reduce power.

The assignee of the Meinke patent, Karl Storz Endoscopy-America, Inc., has not, to this day, offered a monitored or otherwise protected resectoscope that embodies the description contained in the Meinke patent indicating that there were, and continue to be, significant hurdles in the implementation of such a monitored or protected system in a resectoscopic device. The complex design issues of modern resectoscopes and associated surgical techniques have not changed significantly since the Meinke patent and the same problems described therein persist today.

It is thus desirable to overcome the inherent problems associated with incorporating the use of shielded and/or monitored systems such as those disclosed in the prior art into devices such as resectoscopes and hysteroscopes and to give the same, or better, level of protection to patients that is achieved with those prior systems.

Conventional resectoscopes, such as those manufactured by Karl Storz, combine many features into a single device. Such devices are typical of the devices that are predominantly used in many urological and gynecological electrosurgical procedures. It is estimated that approximately 200,000 of the resectoscopic surgeries in the United States alone are performed with a Storz instrument. This represents approximately ⅔ of the total procedures performed each year. U.S. Pat. No. 6,755,826, assigned to Olympus, gives one example of some of the mechanical complexities of a resectoscope. The details of the '826 patent are hereby incorporated by reference into this disclosure in their entirety.

Resectoscopes, such as those manufactured by Karl Storz, involve complex mechanics and generally bulky construction when compared with laparoscopic devices. For example, resectoscopes employ many components, each of which must be used in combination in a single device. In laparoscopic procedures, several separate devices are typically used to perform the many functions of a resectoscope. These include optics, illumination, irrigation (both in and out), electrical function (RF power), and the mechanical linkages for operation of the cutting tools. In addition, user proximity to resectoscopic devices presents its own challenges and increased need to prevent current from energizing the components that are near the surgeons face. Since the surgeon's face is, in many situations can be close to metallic conductive optics, there is the potential for current to flow directly to the surgeon and cause injury.

There are several additional problems that need to be overcome in resectoscopic and like devices that are not addressed in the prior art and that have not been addressed in any currently available technology. For example, the 100 ohm impedance addressed in the Meinke '492 patent is not low enough to completely and/or adequately couple the harmful current away from the patient and the user. While it does cut down the current flow, it is not adequate for shunting fault currents through the return electrode, particularly in applications where instruments have metallic components (e.g., resectoscopic applications). The 100 ohm impedance disclosed in the Meinke '492 patent is meant to prevent alternate return current from flowing through the metal components to the generator return. 100 ohms is not high enough to do that completely and some portion of the total current could still be conducted and may be enough to cause a burn at the contact with wet tissue.

Finally, resectoscopes are subject to otherwise "normal" working element current surges due to blood and/or other conductive fluid tissue bridging the working element and active electrode. These current surges are normally present on only a temporary basis and may or may not represent a dangerous condition to the patient that requires intervention.

Although present devices are functional, they are not sufficiently accurate or otherwise satisfactory. Accordingly, an improved system and method are needed to address one or more of the various shortfalls of present technology and to provide other new and innovative features.

SUMMARY OF THE INVENTION

Exemplary embodiments of the present invention that are shown in the drawings are summarized below. These and other embodiments are more fully described in the Detailed Description section. It is to be understood, however, that there is no intention to limit the invention to the forms described in this Summary of the Invention or in the Detailed Description. One skilled in the art can recognize that there are numerous modifications, equivalents and alternative constructions that fall within the spirit and scope of the invention as expressed in the claims.

In one embodiment, the invention may be characterized as a method for performing an electrosurgical procedure on a patient. The method in this embodiment includes obtaining information indicative of at least one physical characteristic of the patient and generating a reference voltage that is derived, at least in part, from the information. The reference voltage is coupled to a body of the electrosurgical apparatus and the reference voltage is generated to a level so as to limit any difference between a voltage of the patient and a voltage of the body of the electrosurgical apparatus.

In another embodiment, the invention may be characterized as an electrosurgical apparatus comprising a connector block configured to detachably couple with an active electrode assembly. The connector block in this embodiment includes a shield contact disposed so as to be capable of detachably coupling with a shield of the active electrode assembly and an active electrode contact disposed so as to be capable of detachably coupling with an active electrode of the active electrode assembly. The electrosurgical apparatus also includes a conductive body coupled to the connector block. The conductive body is positioned relative to the connector block such that when the active electrode assembly is coupled to the connector block, a temporary, yet tolerable, conduction between the active electrode and the conductive body may occur during an electrosurgical procedure.

In yet another embodiment, the invention may be characterized as an active electrode assembly for use in an electrosurgical apparatus. The active electrode assembly in this embodiment includes an active electrode with a tip configured to impart a voltage to a region of a patient so as to carry out an electrosurgical procedure at the region. The electrode assembly also includes a layer of insulation surrounding the active electrode and a shield surrounding the insulation. The shield in this embodiment is configured so as to be capable of detachably and conductively coupling with a shield lead of the electrosurgical apparatus.

As previously stated, the above-described embodiments and implementations are for illustration purposes only. Numerous other embodiments, implementations, and details of the invention are easily recognized by those of skill in the art from the following descriptions and claims.

BRIEF DESCRIPTION OF THE DRAWINGS

Various objects and advantages and a more complete understanding of the present invention are apparent and more readily appreciated by reference to the following Detailed Description and to the appended claims when taken in conjunction with the accompanying Drawings wherein:

DETAILED DESCRIPTION

Figure 1:
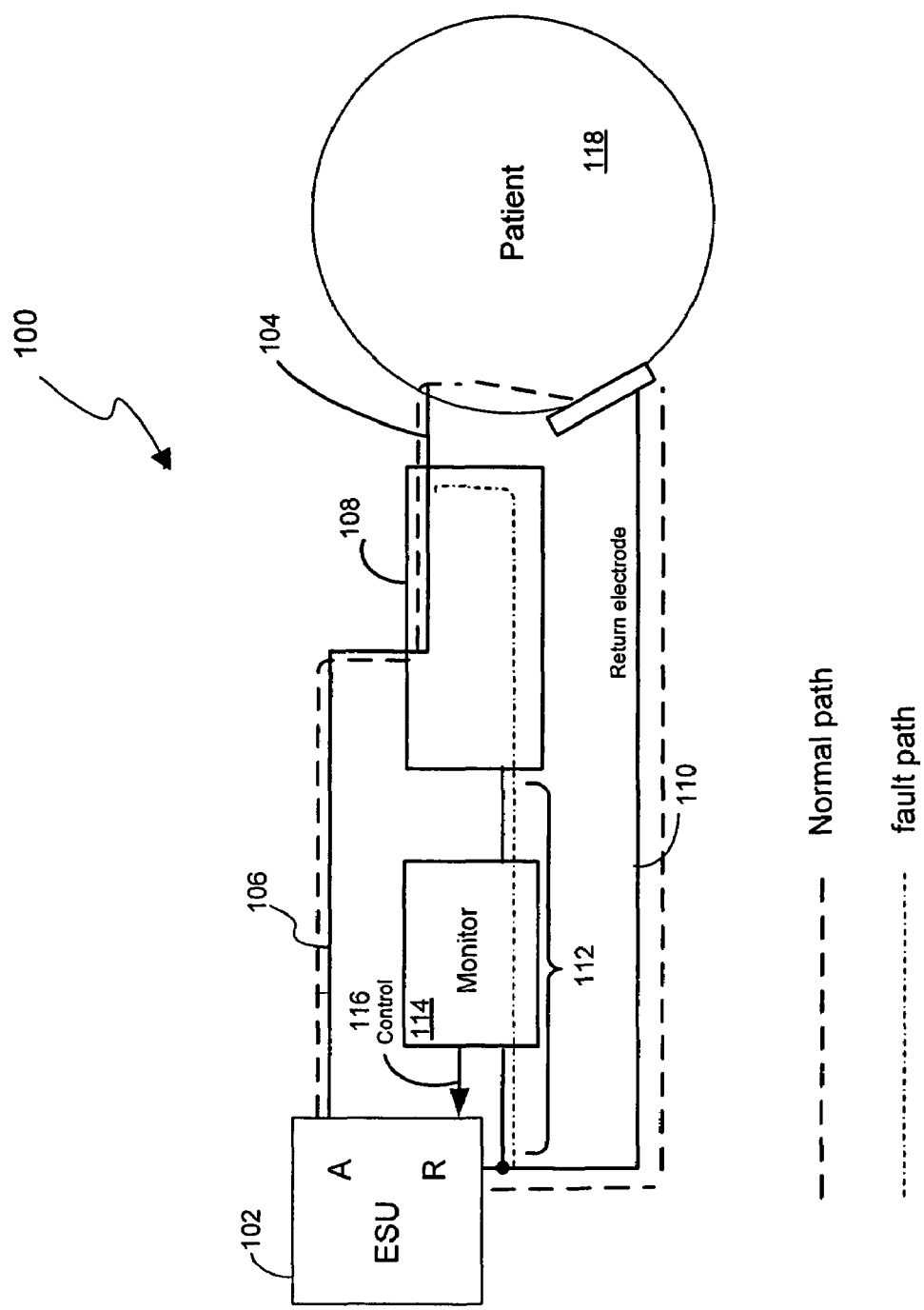
FIGS. 1 and 2 are block diagrams depicting one embodiment of a system for monitoring an electrosurgical procedure.

Referring now to the drawings, where like or similar elements are designated with identical reference numerals throughout the several views, FIG. 1 illustrates a block diagram of one embodiment of a system 100 for monitoring an electrosurgical procedure. As shown, a generator 102 is coupled to an active electrode 104 via an active line 106, and a conductive body 108 that supports the active electrode 104 is shown coupled to a return electrode 110 of the generator 102 via a low impedance path 112.

As depicted in FIG. 1, the low impedance path 112 includes a monitor 114 that is coupled to the generator 102 with a control line 116. The active electrode 104 and the return electrode 110 are shown contacting a patient 118 so as to create a normal current path that is shown running from the generator 102, through the active line 106, active electrode 104, the patient 118 and the return electrode 110 back to the generator 102. Also shown is a fault current path that runs from a portion of the active electrode 104, through the conductive body 108 and the low impedance path 112.

The generator 102 in the exemplary embodiment is a high frequency electrosurgical generator capable of generating radio frequency current in the range of 50 KHz to 5 MHz, but the type of generator implemented may vary depending upon the type of electrosurgical procedure being performed. Examples of high frequency generators include the ERBE ICC 350 electrosurgical generator available from ERBE Elektromedizin, Tubingen, Germany and the FORCE-2 and FX electrosurgical generators available from VALLEYLAB of Boulder, Colo.

The monitor 114 in this embodiment is implemented with a low impedance monitor configured to measure current and/or voltage in the fault current path. The impedance of the monitor 114 in several embodiments is substantially less than 100 Ohms, and in other embodiments the impedance is less than or equal to about 50 Ohms. In yet other embodiments, the impedance of the monitor 114 is less than or equal to about 30 Ohms. An exemplary monitor that has an impedance of about 20 Ohms is an EM-2 style monitor manufactured by Encision, Inc of Boulder Colo., but it is contemplated that the monitor 114 may be implemented with an impedance of less than or equal to about 15 Ohms.

In several embodiments, the conductive body 108 is a portion of an electrosurgical apparatus (e.g., an endoscope) that is not intended to impart surgical-level voltages (e.g., voltages that ablate tissue) to the patient; yet the conductive body 108 is susceptible (or even intended) to contact the patient during an electrosurgical procedure. In many embodiments, the conductive body 108 provides mechanical support for elements of the surgical apparatus. For example, the active electrode 104 is generally supported, yet electrically insulated from, the conductive body 108. Although conductive bodies of surgical instruments are frequently discussed herein in the context of endoscopes for exemplary purposes, it should be recognized that the conductive bodies described herein may be realized in a variety of electrosurgical apparatus including endoscopes, colonoscopies, laproscopic instruments and catheter systems.

The active electrode 104 in the exemplary embodiment imparts a voltage, also referred to herein as an electrical potential, generated by the generator 102 to the patient 118. In some embodiments 104 the active electrode 104 includes a rollberball configuration and in other embodiments a cutting loop, but other embodiments are certainly contemplated and are well within the scope of the present invention.

In operation, when a potential is applied to the patient 118 with the active electrode 104, a current, following the normal current path, flows from the active electrode 104, through the patient 118 to the return electrode 110, which is coupled to another portion of the patient 118. In several embodiments, the current alters (e.g., ablates) tissue of the patient 118 that is within and around the normal current path so as to effectuate a surgical procedure.

During an electrosurgical procedure, one or more events can cause the potential of the conductive body 108 to approach the potential of the active electrode 104. For example, if the insulation surrounding the active electrode 104 fails, the impedance between the conductive body 108 and the active electrode 104 will decrease and may allow current to flow (e.g., arc) from the active electrode 104 to the conductive body 108. In addition, during some electrosurgical procedures, conductive fluids and/or tissue are prone to accumulate between the active electrode 104 and the conductive body 108. These conductive fluids also reduce the impedance between the active electrode 104 and the conductive body 108, which allows current to flow, via the conductive fluid, from the active electrode 104 to the conductive body 108.

In accordance with several embodiments of the present invention, the low impedance path 112 effectively shunts current from the conductive body 108 to the return electrode 110 so as to prevent the conductive body 108 from reaching a much higher potential. In this way, the conductive body 108 is prevented from attaining a level of potential that would otherwise be harmful to the patient. In some embodiments where the conductive body 108 forms part of an endoscope for example, portions of the conductive body 108, telescope (not shown), and sheath (not shown) routinely contact the patient, and if current is not shunted away from the patient 118, current from these portions of the surgical tool can severely burn the patient 118 at unintended locations.

As depicted in FIG. 1, when an event occurs that causes the potential of the conductive body 108 to approach that of the active electrode 104, fault current following the fault path flows from the conductive body 108 through the low resistance path 112 to the return electrode 110. In accordance with several embodiments of the present invention, the low impedance path 112 has an impedance that is substantially less than 100 Ohms.

Figure 2:
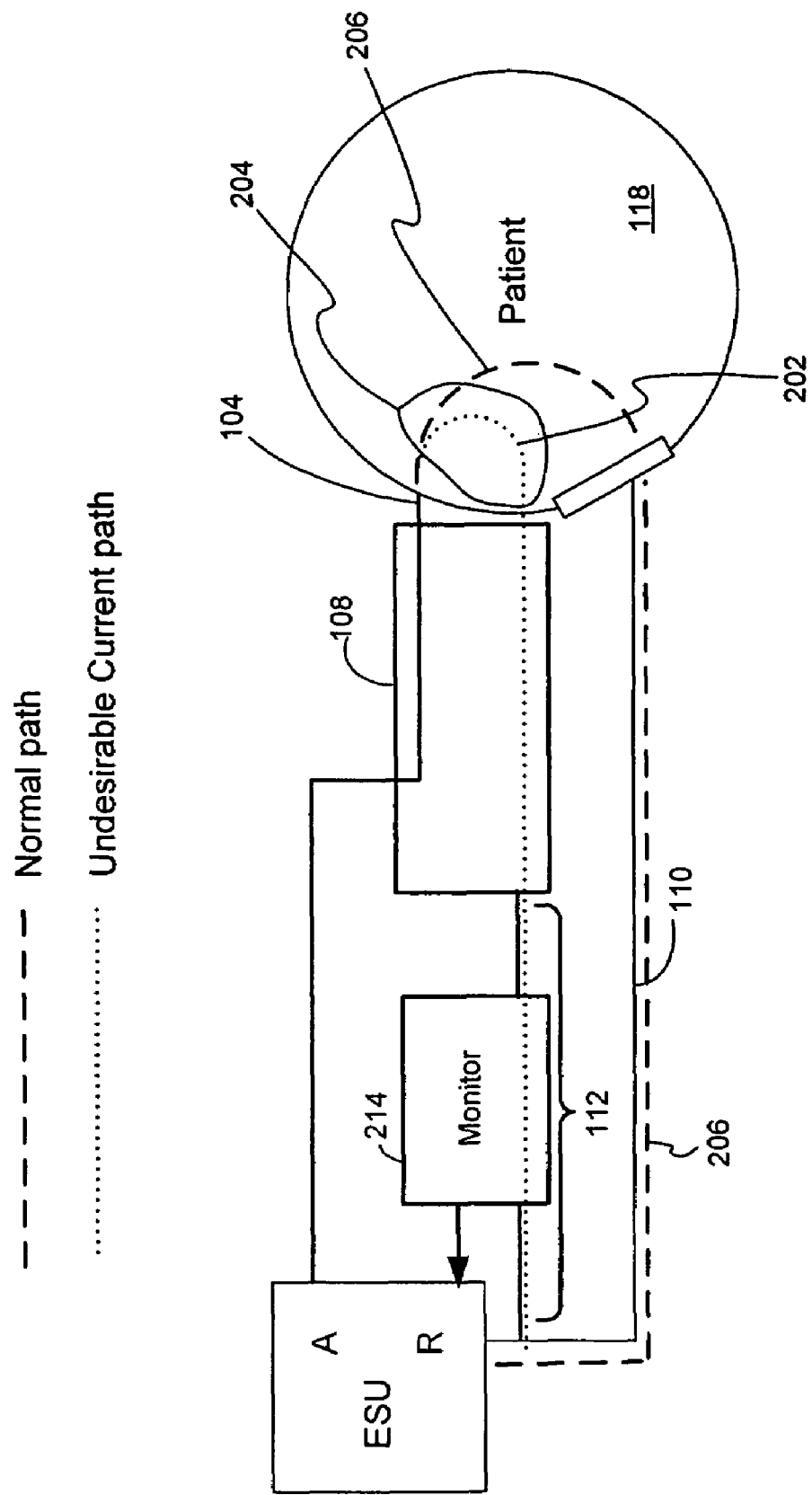

Creating a low impedance path between the conductive body 108 and the return electrode 110, however, may create an undesirable current path 202 from the active electrode 104 to the return electrode 110 that includes unintended portions 204 of the patient 118. Specifically, as shown in FIG. 2, the combined impedance of the low impedance path 112, the conductive body 108 and the unintended portions 204 of the patient 118 is low enough to attract a harmful level of current through the undesirable current path 202.

As a consequence, in accordance with several embodiments of the present invention, undesirable current that would otherwise flow in the undesirable current path 202 is limited so as to prevent undesirable current from harming the patient 202. In other words, the undesirable current that would otherwise flow from the active electrode 104 to the return electrode 110 through the patient 118, conductive body 108 and the low impedance path 112 is limited.

Figure 3:
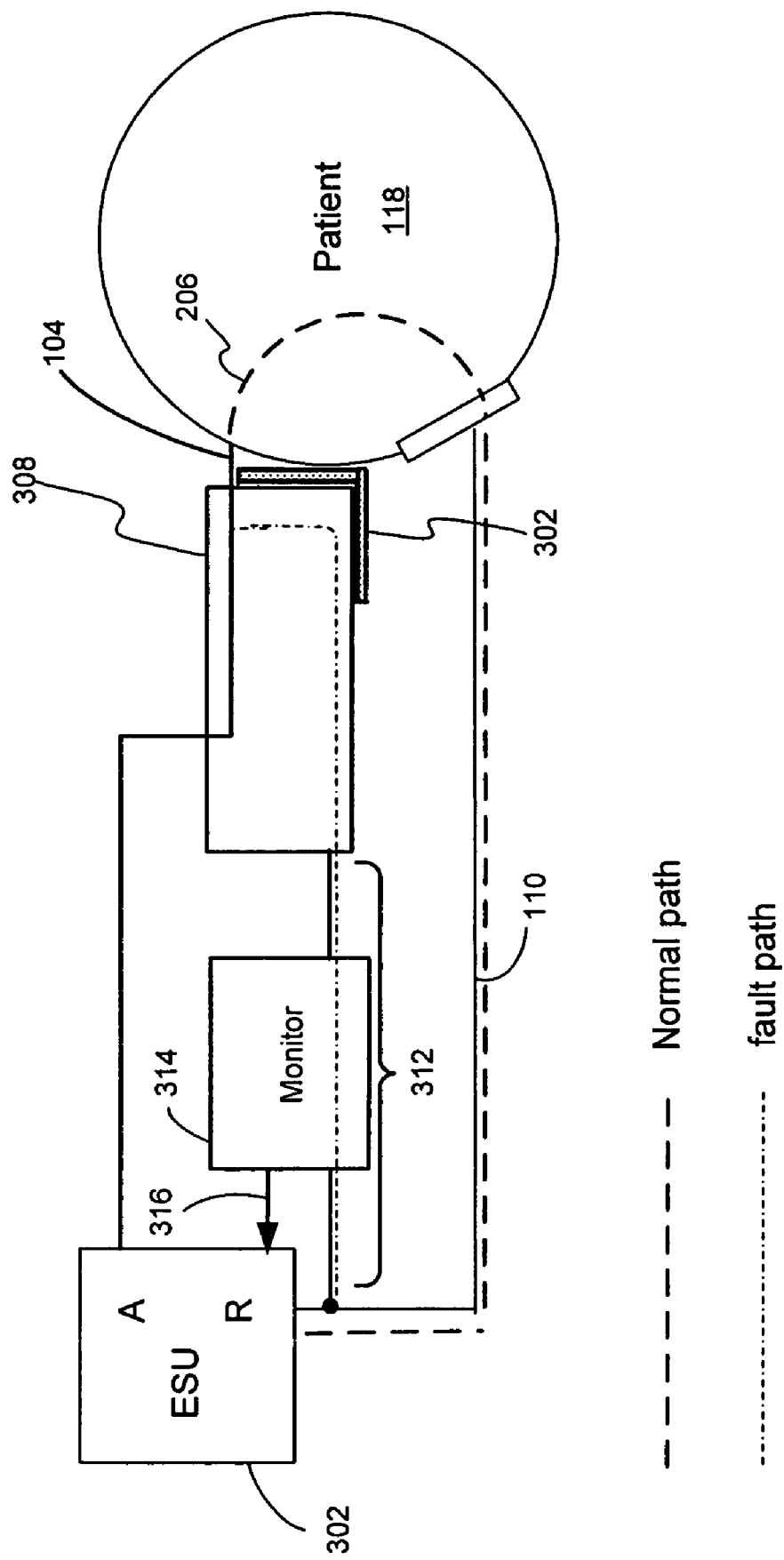
FIG. 3 is a block diagram depicting another embodiment of a system for monitoring an electrosurgical procedure.

FIG. 3 depicts one embodiment of the present invention that limits the undesirable current that would otherwise flow in the undesirable current path 202 described with reference to FIG. 2. In the exemplary embodiment depicted in FIG. 3, an insulator 302 is interposed between the conductive body 308 and the patient 118 so as to limit the amount of current that may flow from the active electrode 104 in the undesirable path 202, which includes the patient 118, the conductive body 308 and the low impedance path 312.

In one embodiment where the conductive body 308 is part of an endoscope for example, the insulator 302 is an insulating sheath that is added to the endoscope so as to be interposed between the patient 118 and the conductive body 308 during an electrosurgical procedure.

Figure 4:
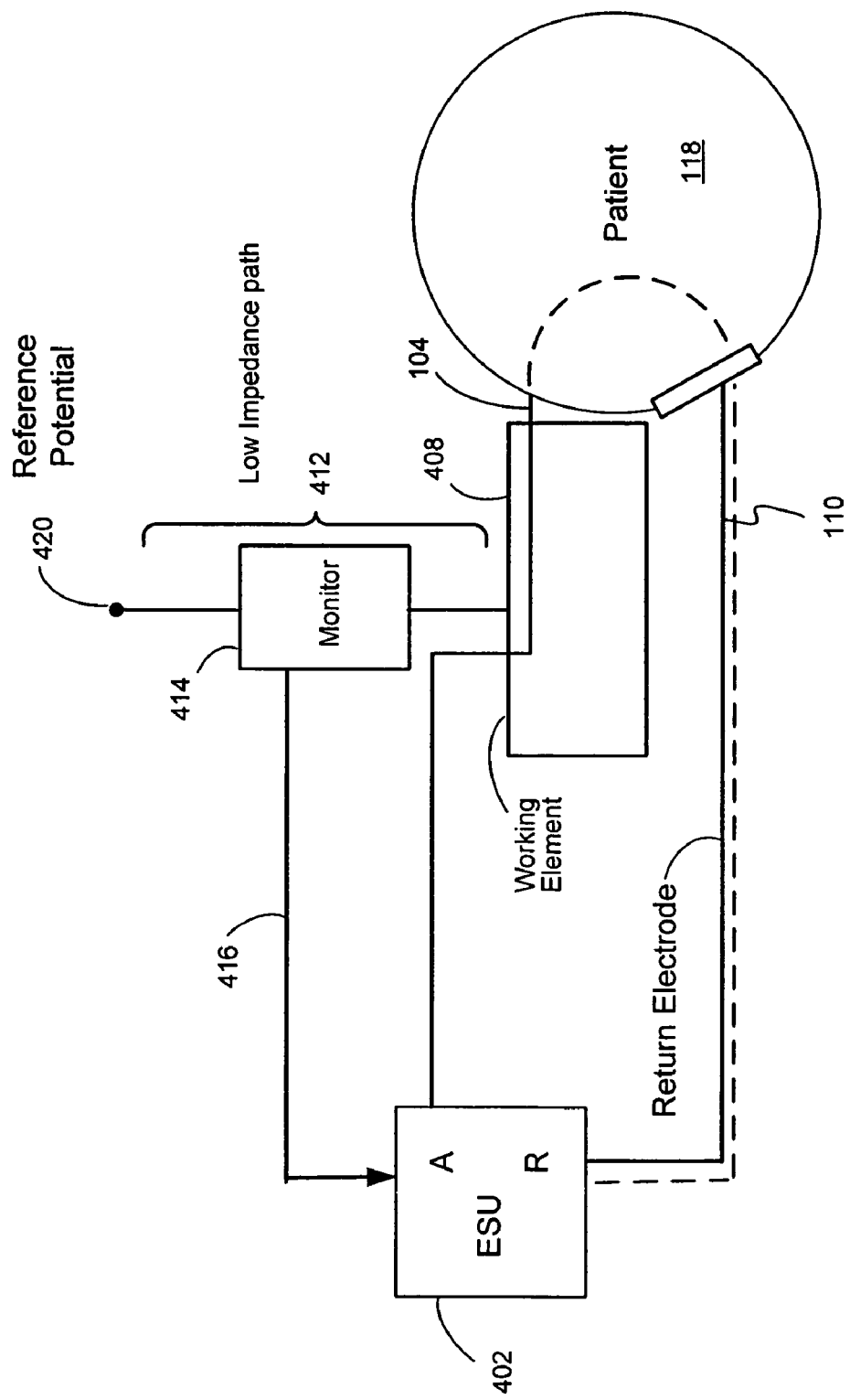
FIG. 4 is a block diagram depicting yet another embodiment of a system for monitoring an electrosurgical procedure.

In another embodiment, the undesirable current is limited by limiting a difference between a voltage of the conductive body 108, 308 and a voltage of the patient 118. Referring to FIG. 4, for example, shown is an exemplary embodiment in which a conductive body 408 is coupled to a reference potential 420 via a low impedance path 412. In the exemplary embodiment the reference potential 420 has a voltage that is established so as to render the voltage of the conductive body 408 to be substantially the same as the voltage of the patient 118. In this way, any currents that do travel from the active electrode 104, through the patient 118 to the conductive body 418 are much less likely to cause damage to tissues of the patient 118.

Advantageously, the exemplary configuration depicted in FIG. 4 enables an electrosurgical instrument to be utilized without insulating exterior portions of the instrument from the patient. In the context of resectoscopes, for example, a metallic sheath may be utilized because the conductive body 408 has a potential, by virtue of being coupled to the patient 118 via the low impedance path 412, that is close to the potential of the patient 118.

As a consequence, manufacturers of resectoscopes need not retool to accommodate an insulating sheath, and metallic sheaths often times have a longer life span and smaller size than insulating sheaths. Moreover, most surgeons are accustomed to and prefer the look and feel of stainless steel components.

In some variations of the embodiment depicted in FIG. 4, the reference potential 420, in connection with the low impedance path 412, maintains the conductive body 408 at a potential that is within 25 Volts of the potential of the patient. In other variations, the potential of the conductive body 408 is maintained to within 15 Volts of the patient. In yet other variations, the potential of the conductive body 408 is maintained to within 10 Volts of the patient potential, and in accordance with still other variations, the reference potential 420 is varied so as to maintain the potential of the conductive body to within 3 Volts of he conductive body 408.

As depicted in FIG. 4, a protective circuit advantageously utilizes a separate reference potential 420, which lacks a voltage offset (i.e., a substantially lower voltage than a patient voltage) that is inherent with a return electrode (e.g., the return electrode 110). As a consequence, currents that would ordinarily flow from the active electrode 104 through an undesirable path that includes the patient 118 and the conductive body 408 are substantially reduced or prevented altogether. Thus, any tissue of the patient 118 or the operator/surgeon that contacts the conductive body 408 is protected from being a part of the undesirable current path.

Moreover, because the conductive body 408 is coupled to the reference potential 420 (i.e., via the low impedance path 412) instead of the return electrode 110, this embodiment is aligned with international standards such as IEC 601-2-2. This in turn may allow the use of a metallic sheath as a alternate to an insulated sheath. This is desirable because it comports with the user's customary instruments, it is durable, and aids in achieving a minimum instrument diameter.

It should be recognized that the embodiments described with reference to FIG. 4 are certainly not limited to applications involving endoscopes. For example, coupling the conductive body (e.g., working element) of a variety of electrosurgical devices (e.g., colonoscopes and catheter systems) to the reference potential 420 via the low impedance path 412 is advantageous for one or more of the reasons discussed above.

Although embodiments described with reference to FIG. 4 do have advantages over embodiments described with reference to FIG. 3, it should be recognized that the embodiments described with reference to FIG. 3 do provide a viable approach to improving the safety of electrosurgical procedures.

While referring to FIGS. 3 and 4, simultaneous reference will be made to FIG. 5, which is a flowchart depicting steps traversed in accordance with one method for performing an electrosurgical procedure. As shown, the active electrode 104 is initially applied to the patient 118 along with the return electrode 110 so as to create a current path 206 in tissue of the patient 118 between the active electrode 104 and the return electrode 110 (Blocks 500-506).

In addition, the conductive body 308, 408 is coupled to a reference voltage with a low impedance path. (Block 508). In the embodiment depicted in FIG. 3, the reference voltage is the voltage of the return electrode 110, and in the embodiment of FIG. 4, the reference voltage is the voltage of the reference potential 420.

Figure 5:
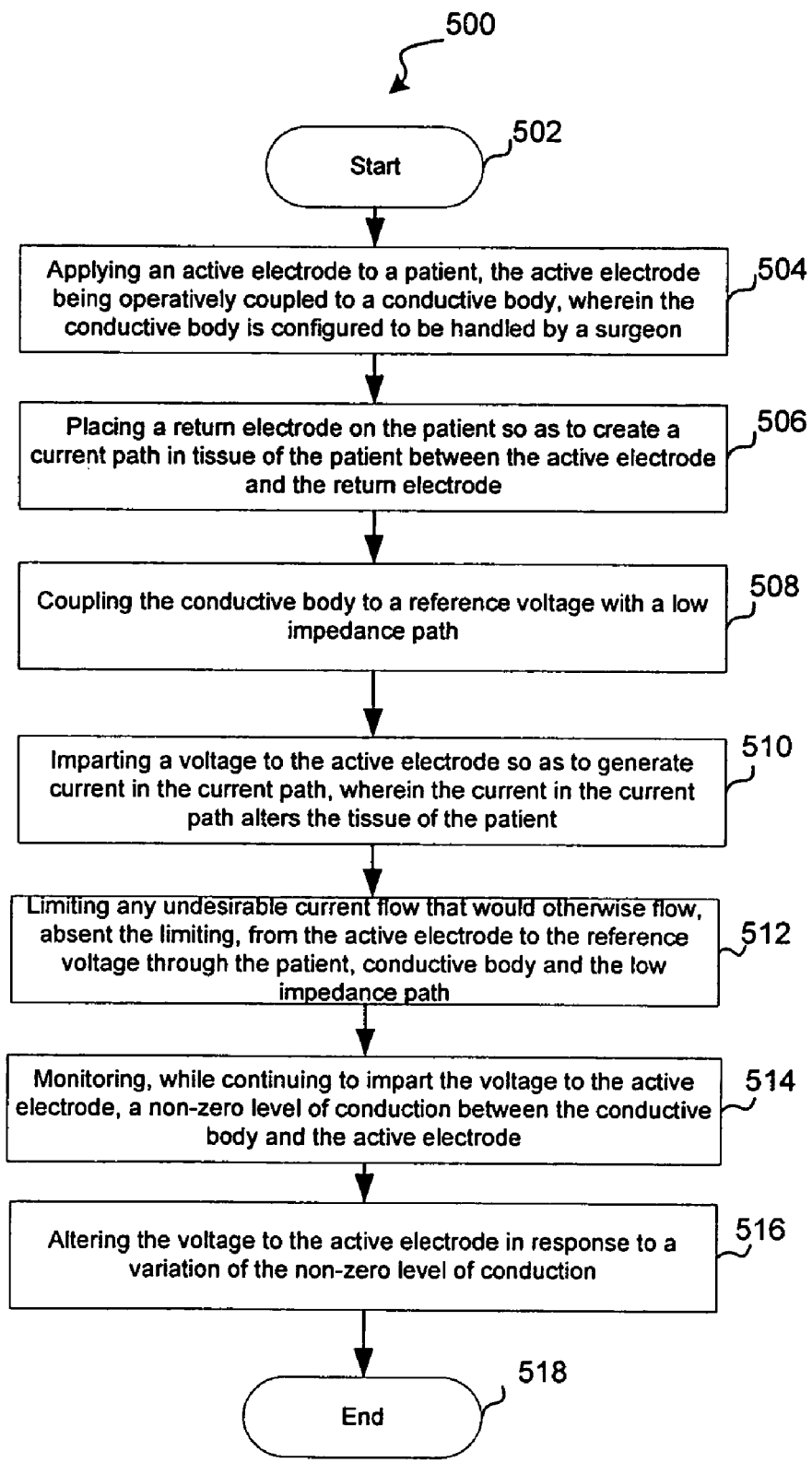
FIG. 5 is a flowchart depicting steps carried out in accordance with an electrosurgical procedure.

As shown in FIG. 5, a voltage is then imparted to the active electrode 104 so as to generate current in the current path 206 that alters tissue of the patient 118 (Block 510). While the voltage is imparted to the active electrode 104, any undesirable current 202 that would otherwise flow from the active electrode 104 to the reference voltage 110, 420 through the patient 118, conductive body 308, 408 and low impedance path 312, 412 is limited (Block 512).

Additionally, in several embodiments, a non-zero level of conduction between the conductive body 308, 408 and the active electrode 104 is monitored while continuing to impart the voltage to the active electrode 104 (Block 514), and the voltage of the active electrode 104 is altered in response to a particular variation of the non-zero level of conduction between the conductive body 308, 408 and the active electrode 104 (Blocks 516, 518).

In many embodiments, variations in the level of conduction between the active electrode 104 and the conductive body 308, 408 are tolerated for one or more periods of time. For example, when the electrosurgical procedure depicted in FIG. 5 is carried out with either a resectoscope or hysteroscope, chips of tissue and/or blood can cause a temporary conduction between the active electrode 104 and the conductive body 308, 408. Although the patient 118 and operator may need protection from this condition, in these embodiments, such a temporary conduction is not a fault condition per se that requires the generator 302, 402 to be shut down completely. As a consequence, the monitor 314, 414 in some embodiments responds to the temporary conduction with a signal 316, 416 that does not immediately shut down the generator.

For example, in some embodiments the monitor 314, 414 provides a warning to the operator without initiating a reduction of power to active electrode. In other embodiments, the particular variation that causes an alteration of the current level between the active electrode 104 and the conductive body 308, 408 is a particular current level that is sustained for a predetermined amount of time. The alteration to the voltage imparted to the active electrode 104 in some embodiments is a reduction in the voltage applied to the active electrode 104 so that the energy level is brought to a level that the patient's body can tolerate without harm. In yet other embodiments, the alteration to the voltage imparted to the active electrode 104 is a complete removal of the voltage imparted to the active electrode.

In several embodiments, the monitoring for any conduction between the conductive body 308, 408 and the active electrode 104 is carried out by metering a parameter that has a value that varies with the conduction between the conductive body 308, 408 and the active electrode 104. In some embodiments for example, the conduction between the conductive body 308, 408 and the active electrode 104 is carried out by metering the level of current in the low impedance path 312, 412. In other embodiments, the monitoring for conduction between the conductive body 308, 408 and the active electrode 104 is carried out by metering a voltage of the conductive body 308, 408. In these embodiments, the monitoring includes an indirect measurement of the current flowing between the active electrode 104 and the conductive body 308, 408.

The reference potential 420 in some embodiments is generated based upon a voltage known to be close to a typical human voltage. In other embodiments, the reference potential is derived from at least one physical characteristic of the patient.

Figure 6:
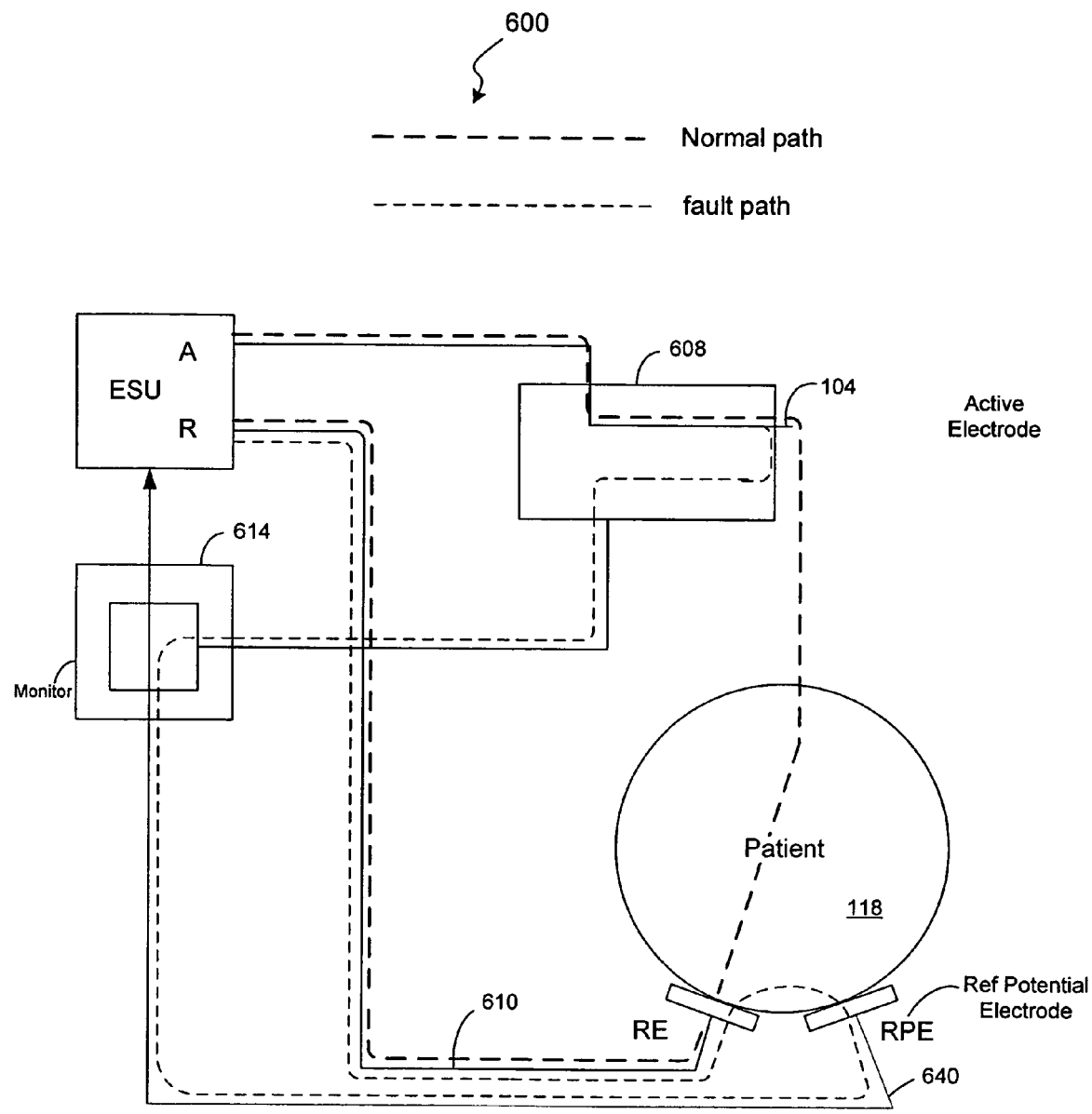
FIG. 6 is a block diagram depicting one embodiment of a system for monitoring an electrosurgical procedure in which the reference potential depicted in FIG. 4 is derived from a voltage of a patient.

Referring next to FIG. 6, for example, shown is a block diagram 600 depicting one embodiment in which the reference potential 420 is derived directly from a voltage of the patient. As depicted in FIG. 6, a conductive body 608 is connected through a monitor 614 to a reference potential electrode (RPE) 640. The RPE 640 in this embodiment is maintained at a reference potential that is consistent with the a potential of the patient's 618 body. In this embodiment, the coupling between the conductive body 608 and the RPE 640, which includes the monitor 614, creates a low impedance path (e.g., less than 100 Ohms) from the conductive body 608 to a reference potential 640, which in this embodiment, is obtained from a direct coupling of the RPE 640 to the patient 118.

The RPE 640 in some embodiments is realized as a completely separate electrode that is coupled to an opposite or alternate site of the patient 118, and in other embodiments the RPE 640 is implemented as a separate conductive area or areas in a return electrode assembly. In both of theses types of implementations, the RPE 640 and the return electrode 610 each have a separate contact area on the patient 118 that electrically isolates, to a substantial degree, the RPE 640 and return electrode 610. Exemplary electrodes that are suitable for implementation as either the return electrode 610 or the RPE 640 are disclosed in U.S. Pat. Nos. 4,416,276 or 4,416,277, the details of which are hereby incorporated by reference into the present application.

Figure 7:
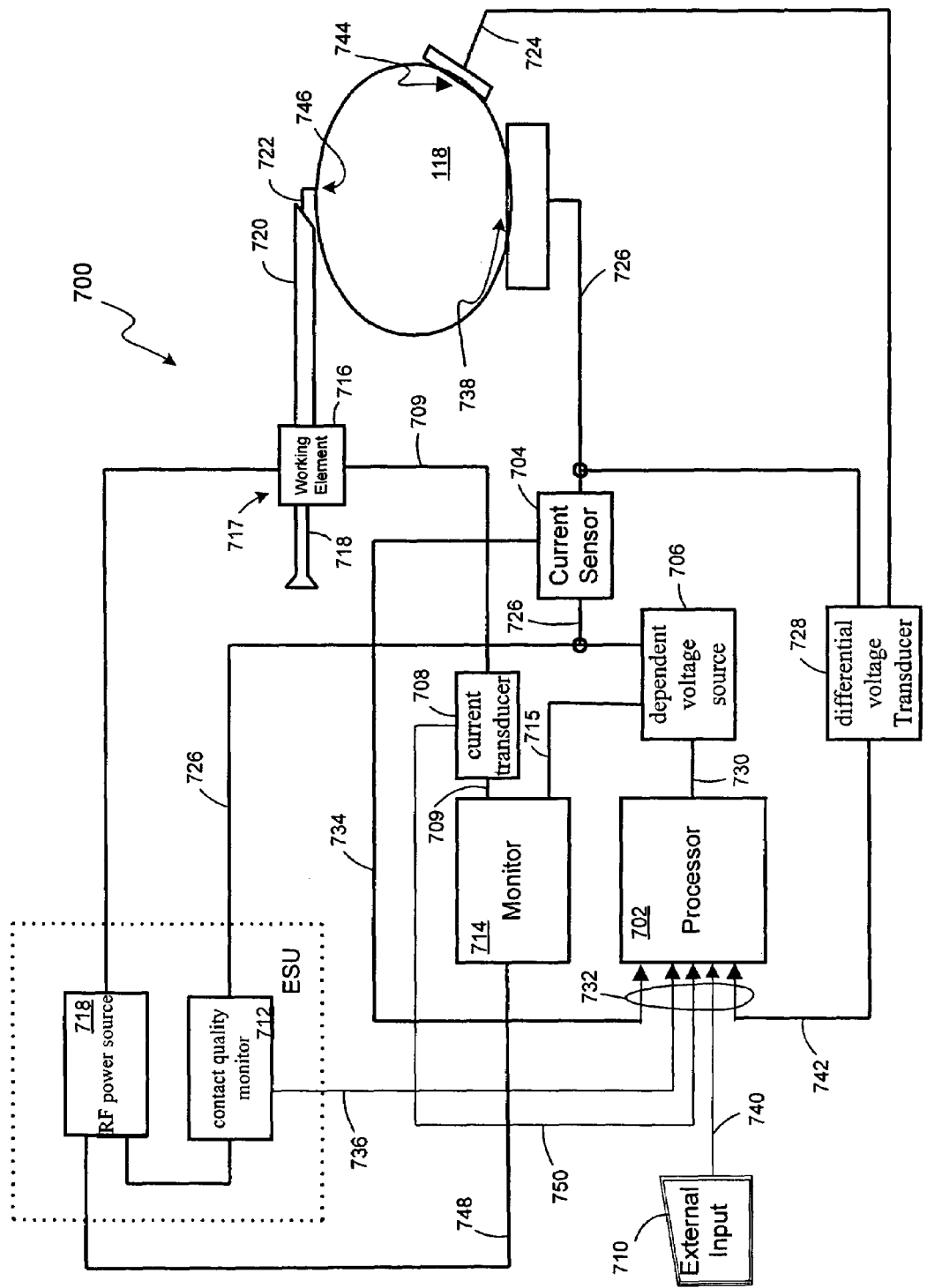
FIG. 7 is a block diagram depicting an embodiment of another system for monitoring an electrosurgical procedure in which the reference potential depicted in FIG. 4 is generated.

Referring next to FIG. 7, shown is a block diagram depicting an exemplary electrosurgical system 700, which is configured to generate a derived reference. As depicted in FIG. 7, a processor 702 is coupled to a current sensor 704, a dependent voltage source 706, a current transducer 708, an external input 710 and a contact quality monitor 712. Also shown is a monitor 714 that is coupled to a conductive body 716, an RF power source 718, and via a derived reference line 715, to the dependent voltage source 706. The conductive body 716 in this embodiment is a working element that forms part of an endoscope 717, which includes a telescope 718, a tube assembly 720 and an active electrode 722. As depicted in FIG. 7, the active electrode 722 is in contact with the patient 118. In addition, a reference electrode 724 and return electrode 726 are shown coupled to the patient 118 at different locations of the patient 118. The reference electrode 724 is shown coupled to a differential voltage transducer 728 and the return electrode 726 is shown coupled to a current sensor 704 (e.g., via inductive coupling).

The processor 702 in several embodiments includes analog and digital components and a variable gain amplifier (not shown). One of ordinary skill in the art will recognize, however, that the processor 702 may be realized in other embodiments as an entirely analog or entirely digital processor and may be one integrated processor (e.g., an ASIC or PIC controller) or several discrete components. In the present embodiment, the analog and digital components control the variable gain amplifier so as to provide an output 730 to the dependent voltage source 706, which affects the derived reference voltage 715 that is generated by the dependent voltage source 706.

The output 730 of the processor, and hence, the derived reference voltage 715 of the dependent voltage source 706 is a function of one or more of the inputs 732 to the processor 702. In particular, the processor 702 receives a signal 734 from the current sensor 704 (e.g., a current transducer), which is indicative of a level of current in the return line 726. The processor 702 then scales the signal 734 from the current sensor 704 as a function of other inputs 736, 740, 742 to the processor 702. In several embodiments, the processor 702 continuously receives the inputs 732 and adapts the output 730 to the changing conditions/of the patient 118.

As depicted in FIG. 7, one of the inputs 732 to the processor 702 is a signal 736 from the contact quality monitor 712, which is indicative of an impedance of the patient 118 at a location 738 where the return electrode 726 contacts the patient. In this embodiment, the return electrode 726 includes two return wires (not shown), and each of the return wires is separately coupled to the patient 738. The contact quality monitor 712 in the present embodiment meters an impedance of the patient 118 between the two return wires, and provides the signal 736 to the processor 702.

Another input to the processor 702 in the exemplary embodiment is the external input 710. Although the external input 710 is depicted as a single line for simplicity, in some embodiments the external input is realized by multiple inputs to the processor 702. In this embodiment, the external input is a signal 740 that is indicative of one or more variables such as an amount of body fat in the tissue of the patient 118, the particular portion of the patient 118 being operated upon and information about the locations on the patient 118 where the electrodes 724, 726 are being placed. These factors are merely exemplary, however, and other factors may be utilized by the processor 702 as well.

Yet another input to the processor 702 in the exemplary embodiment is a signal 742, which is indicative of a difference between the voltage of the return electrode 726 and a voltage of the reference electrode 724 (i.e., a voltage of the patient 118 at the location 744 where the reference electrode 724 is coupled to the patient 118). In some embodiments, the reference electrode 724 is part of an electrode assembly that includes the return electrode 726, but this is certainly not required, and in other embodiments the return electrode 726 and reference electrode 724 are completely separated.

As depicted in FIG. 7, the differential voltage transducer 728 generates an output 742 that is proportional to the difference between the return electrode 726 and the reference electrode 724. Although depicted as a single functional block, the differential voltage transducer 728 includes a an RMS responding detector that generates the output 742.

In the exemplary embodiment, the dependent voltage source 706 is an isolated amplifier with a differential output 715 that is a function of the output 730 of the processor 702 relative to the voltage of the return electrode 726. In this embodiment, the processor 702 provides the output signal 730 at a level that prompts the dependent voltage source 706 to generate, as the derived reference 715, a voltage between 0 and 50 Volts RMS referred to the voltage of the return line 726.

As shown in FIG. 7, the monitor 714 in this embodiment couples the conductive body 716 to the derived reference 715. The monitor 714 in several embodiments is a low impedance monitor (e.g., less than 100 Ohms) so as to provide a low impedance path 709 between the conductive body 716 and the derived reference 715. In one embodiment, for example, the monitor is an EM-2 style monitor manufactured by Encision, Inc of Boulder Colo. As shown, a current transducer 708 is configured to sense a level of current in the low impedance path 709 and provide an output 750 to the processor 702 that is indicative of the level of current in the low impedance path 709. One of ordinary skill in the art will recognize that the current transducer 708 may be realized by a variety of current transducers.

In some embodiments, the processor 702 generates the output 730 at a level that translates to a derived reference voltage 715 that is substantially the same as a voltage of the patient 118 at the surgical site 746. In this way, the voltage of the conductive body 716 relative to the surgical site of the patient 746 is limited to a relatively small value (e.g., less than 25 Volts) that is a function of the current in the low impedance path 709 from the conductive body 716, through the monitor 714, to the derived reference 715.

In other embodiments, the processor 702 generates the output 730 at a level that translates to a derived reference 715 that compensates for current flow in the low impedance path 709 from the conductive body 716 through the monitor 714 to the derived reference 715 so as to render the voltage of the conductive body 716 at a level that is substantially the same as a voltage of the patient 118 at the surgical site 746.

As shown in FIG. 7 for example, in the event the current level from the conductive body 716, through the monitor 714, to the derived reference 715 increases (indicating a voltage of the conductive body 716 is higher than the patient voltage), the current transducer 708 provides the output 750 to the processor 702 at a level that is indicative of the increased level of current in the monitor 714. In turn, the processor 702 adjusts the output signal 730 to the dependent voltage source 706 so that the derived reference voltage 715 is decreased. In this way, the voltage of the conductive body 716 is also reduced back to the level of the patient at the surgical site 746.

Figure 8:
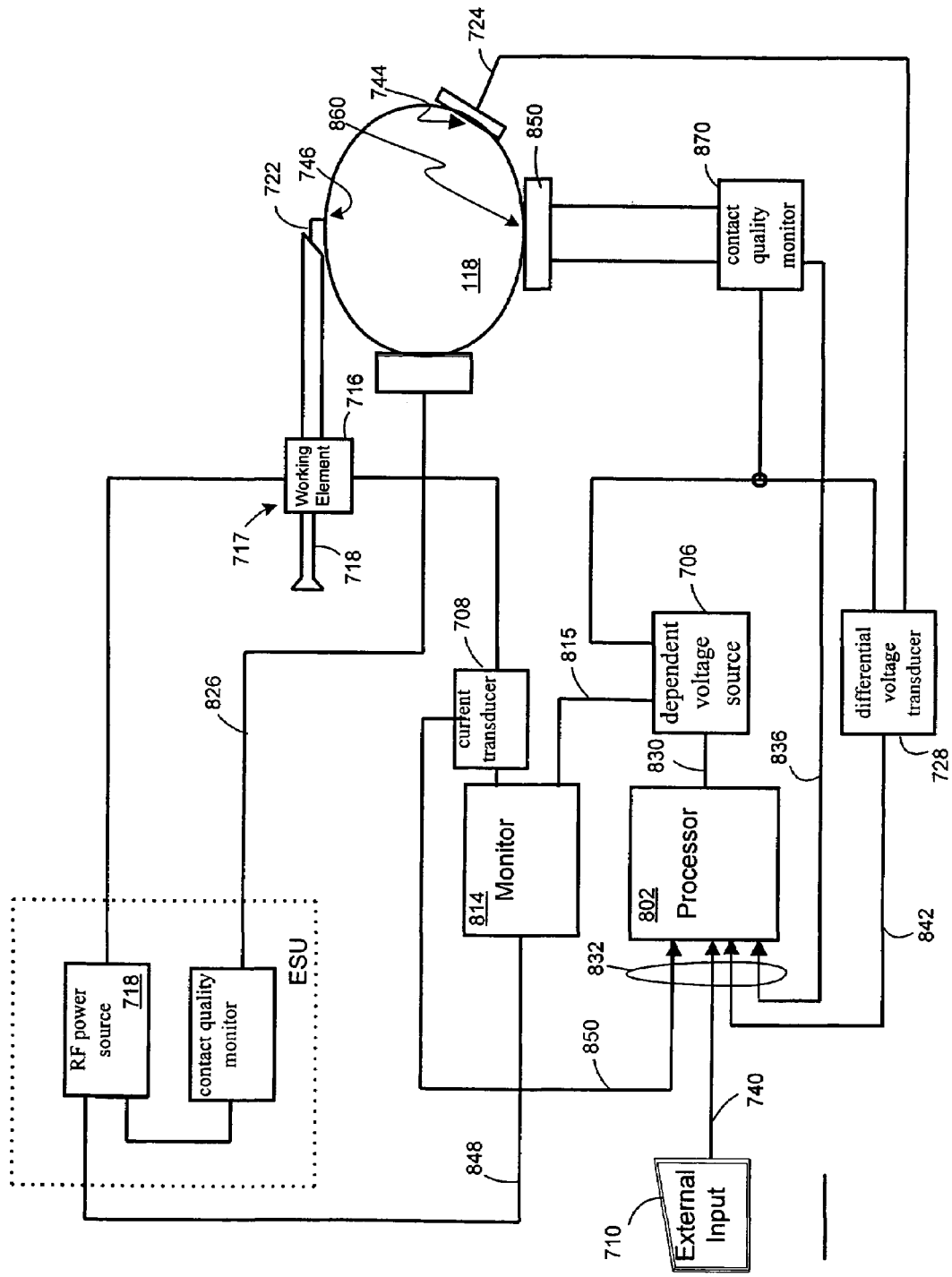
FIG. 8 is a block diagram depicting a variation of the system depicted in FIG. 7.

Referring next to FIG. 8, shown is a block diagram depicting another embodiment of an electrosurgical system 800, which is configured to generate a derived reference 815 utilizing a reference potential electrode 850. The electrosurgical system 800 operates in a similar manner as the system 700 depicted in FIG. 7 except the derived reference 815 in the present embodiment is referenced to a potential of the patient 860 at the reference potential electrode 850 instead of the return electrode 726. In addition, a contact quality monitor 870 in this embodiment provides a signal 836 which is indicative of an impedance of the patient 118 at a location 860 where the reference potential electrode 850 contacts the patient 118. The differential voltage transducer 728 in this embodiment generates an output 842 that is proportional to the difference between the reference potential electrode 850 and the reference electrode 724.

As depicted in FIG. 8, the processor 802 receives and scales the signal 842 from the differential voltage sensor 728 as a function of other inputs 836, 740, 850 so as to generate an output 830 which is converted to the derived reference voltage 815 by the dependent voltage source 706. In several embodiments, the processor 802 continuously receives the inputs 832 and adapts the output 830 to the changing conditions/of the patient 118.

Figure 9:
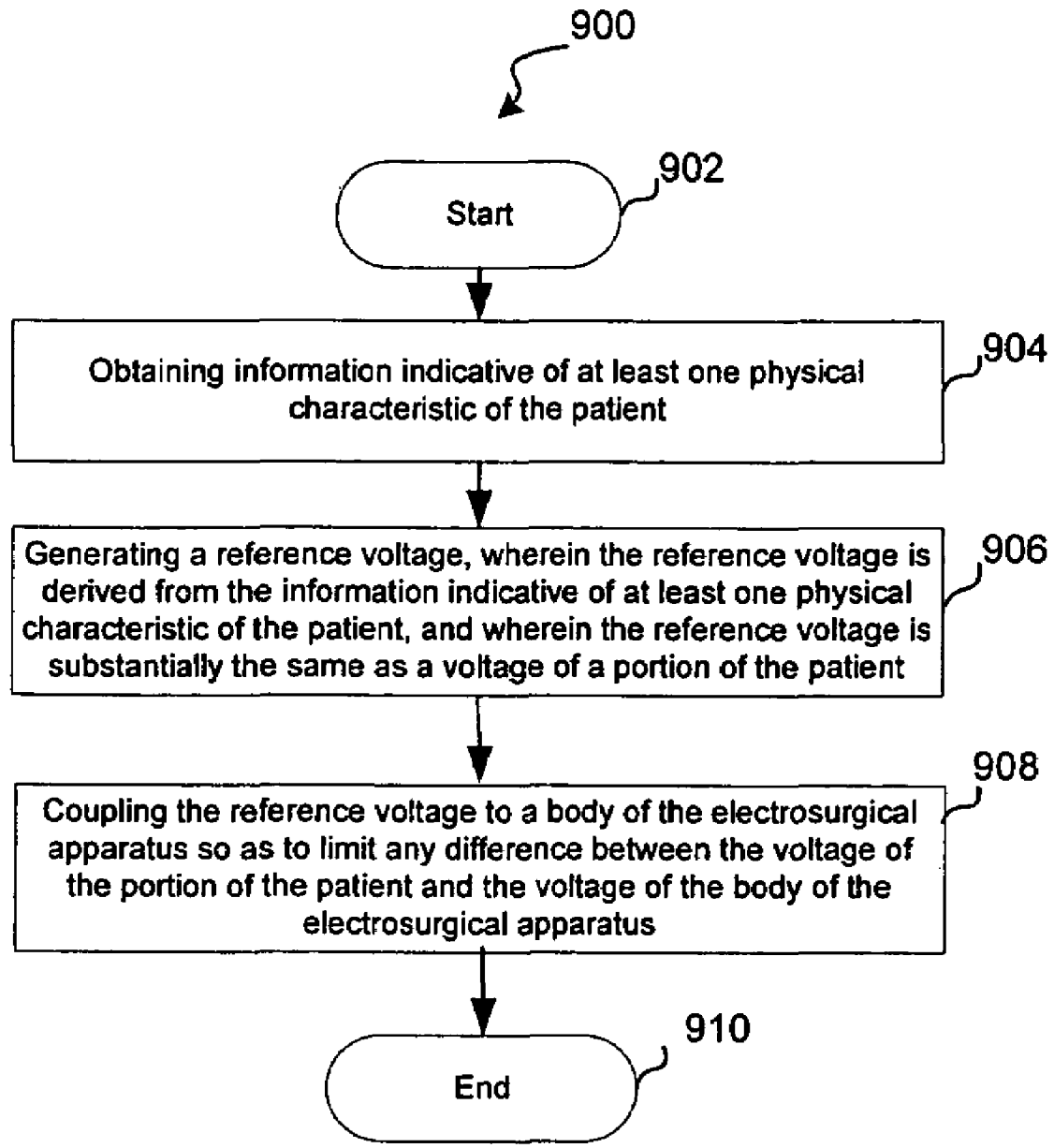
FIG. 9 is a flowchart depicting steps carried out in connection with preparing an electrosurgical apparatus for an electrosurgical procedure in accordance with the embodiment depicted in FIGS. 7 and 8.

Referring next to FIG. 9, shown is a flowchart 900 depicting steps carried out to prepare an electrosurgical instrument for an electrosurgical procedure in accordance with the exemplary electrosurgical systems of FIGS. 7 and 8. In operation, the processor 702, 802 initially receives information indicative of at least one physical characteristic of the patient 118 (Blocks 902, 904).

As depicted in the exemplary embodiments of FIGS. 7 and 8 and discussed above, the processor 702, 802 is configured to receive information indicative of different physical characteristics of the patient from the external input 710, the contact quality monitor 712, 870 and the current transducer 708. The information from the external input 710 may include an indication of fat content in the tissue of the patient, the particular portion of the patient 118 being operated upon and information about the locations on the patient 118 where the electrodes 724, 726, 826, 850 are being placed. The signal 736, 836 from the contact quality monitor 712, 870 is indicative of an impedance of the patient 118 at a location 738, 860 where the return electrode 726, 826 contacts the patient 118. In the embodiment depicted in FIG. 7, the output 742 of the voltage transducer 728 is indicative of a difference between the voltage of the return electrode 726 and a voltage of the patient 118 at the location 744 where the reference electrode 724 is coupled to the patient 118. In the alternative embodiment depicted in FIG. 8, the output 842 of the voltage transducer 728 is indicative of a difference between the voltage of the reference potential electrode 850 and a voltage of the patient 118 at the location 744 where the reference electrode 724 is coupled to the patient 118.

The processor 702, 802 in connection with the dependent voltage source 706, then generates a reference voltage (e.g., the derived reference 715, 815) based upon at least one of the physical characteristics of the patient (Block 906). In the embodiment discussed with reference to FIG. 7, the current signal 734 is scaled by a function that includes, as inputs, the signals 736, 740, 742 from the contact quality monitor 712, the external input 710 and the detector 708, respectively. In the alternative embodiment discussed with reference to FIG. 8, the processor 802 receives and scales the signal 842 from the differential voltage sensor 728 as a function of other inputs 836, 740, 850 so as to generate an output 830 which is converted to the derived reference voltage 815.

The reference voltage (e.g., the derived reference 715, 815) is then coupled to a conductive body (e.g., the working element 716) of the electrosurgical apparatus (e.g., the endoscope 717) so as to limit any difference between the voltage of the surgical site 746 of the patient 118 and the body of the electrosurgical apparatus (e.g., the resectoscope 717) (Blocks 908, 910).

In the embodiments depicted in FIGS. 7 and 8, the monitor 714, 814 provides additional safety by monitoring current flow between the conductive body 716 (e.g., a working element) of the electrosurgical apparatus and the active electrode 722 and alters the level of voltage provided to the active electrode 722 by sending a control signal 748, 848 to the power source 718. In some embodiments, the alteration of the voltage that is applied to the active electrode 722 may be a modulation of the active electrode voltage as a function of one or more characteristics of the current monitored between the active electrode 722 and a conductive body 716 of the electrosurgical instrument (e.g., the resectoscope 717).

As discussed above, in the context of endoscopes, some current is expected to flow between the active electrode 722 and the conductive body 716 while an electrosurgical procedure is being carried out (e.g., due to conductive tissue and/or fluid that becomes interposed between the active electrode 722 and the conductive body 716). As a consequence, in some embodiments, the monitor 714 sends the control signal 748, 848 at a level that directs the power source 718 to continue to impart a voltage to the active electrode 722, for at least an acceptable period of time, while there is a non-zero level of conduction between the active electrode 722 and the conductive body 716. In this way, the electrosurgical procedure is not interrupted due to the expected conduction between the active electrode 722 and the conductive body 716.

Although many variations of the system depicted in FIGS. 7 and 8 are described herein within the context of procedures performed utilizing endoscopes, it is contemplated that generating the derived reference 715 and coupling the derived reference 715 to a conductive body of any one of a variety of electrosurgical devices provides a substantial level of safety by limiting a level of voltage that the body of the electrosurgical devices may attain. It should also be recognized that neither any one nor all of the inputs 732, 832 must be utilized when generating the derived reference 715, 815.

Figure 10:
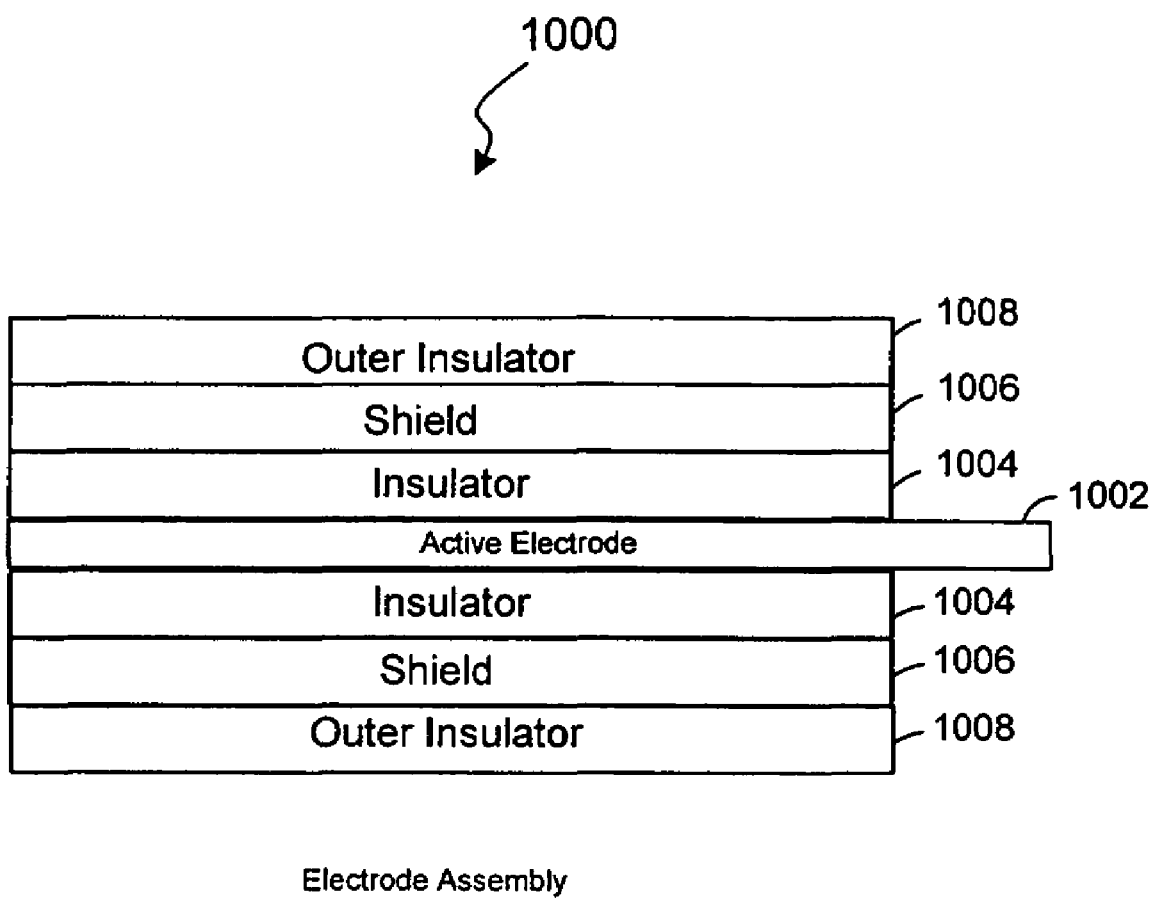
FIG. 10 is a cross sectional view of an exemplary electrode assembly.

Referring next to FIG. 10, shown is a cross sectional view of an exemplary electrode assembly structure 1000, which may be utilized in any of the embodiments described with reference to FIGS. 1-9. As shown, an active electrode 1002 is surrounded in part by an insulator layer 1004, a shield 1006 and an outer insulator 1008 that are stacked in a radial direction relative to the active electrode 1002. The active electrode 1002 in several embodiments is custom designed for implementation as part of the assembly structure 1000. The insulator 1004 in the exemplary embodiment may be composed of a variety of plastics including polyaryletheretherketone (e.g., sold under the PEEK™ brand) and fiber reinforced polymer.

The shield 1006 in this embodiment is a conductive material that may include stainless steel and/or aluminum. As depicted in FIG. 10, the shield is arranged so as to protect the insulator 1004 that surrounds the active electrode 1002 from being pierced. In this way, the shield helps to maintain electrical isolation between a conductive body (e.g., working element) of the electrosurgical device (e.g., an endoscope) that employs the electrode assembly 1000.

Figure 11:
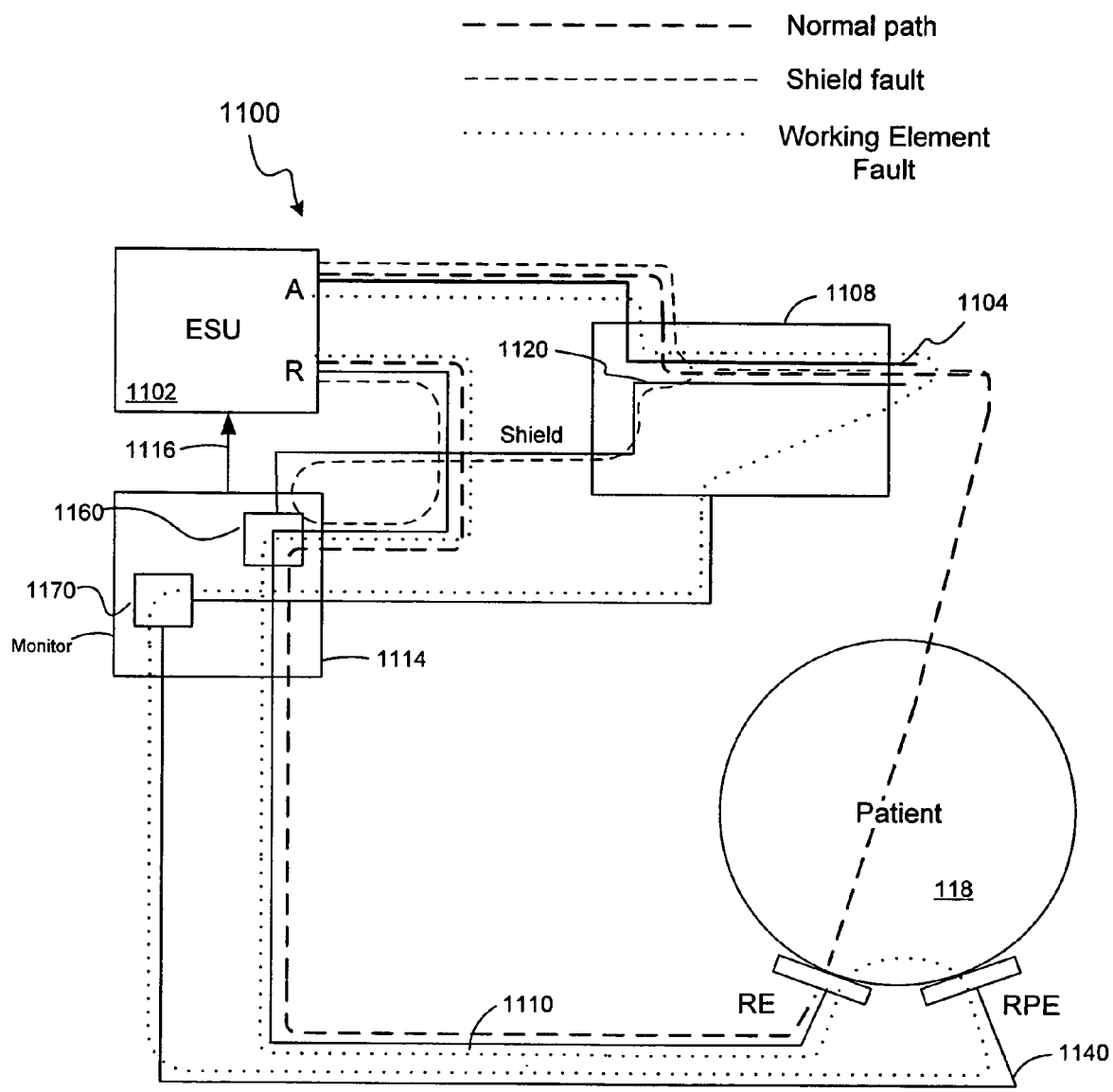
FIG. 11 is a block diagram of a system for monitoring both a conductive body and a shield of the electrode assembly depicted in FIG. 10.

In some embodiments, as discussed further with reference to FIG. 11, the shield 1006 is adapted so as to be capable of being conductively coupled to a monitor, and the monitor is then able to assess the integrity of the electrode assembly by monitoring a level of conduction between the shield 1006 and the active electrode 1002.

As shown, the outer insulator 1008 is disposed so as to insulate the shield 1006 from other components of the electrosurgical device when the electrode assembly 1000 is installed and utilized. The outer insulator 1008 may be realized by similar materials as the inner insulator 1004, but the outer insulator need not have the level of strength nor the low dielectric constant of the inner insulator 1004.

Referring next to FIG. 11, shown is a block diagram of a system 1100 for monitoring both a conductive body 1108 and a shield 1120 of an electrode assembly (e.g., the electrode assembly 1000) during an electrosurgical procedure. In this embodiment the active electrode 1104 incorporates the active-insulation-shield-insulation construction, described with reference to FIG. 10, through an otherwise conventional conductive body 1108.

As depicted in FIG. 11, an RPE 1140 is utilized to provide a reference potential that is derived from a direct coupling of the RPE 1140 to the patient 118. In alternative embodiments, the conductive body 1108 is coupled to a derived reference (e.g., the derived reference 715) that is generated based upon one or more physical characteristics of the patient. The RPE 1140 in the present embodiment may be a completely separate electrode on an alternate site of the patient 118, or it may be a partitioned area in a return electrode assembly.

In this embodiment, the shield component 1120 of the electrode assembly (not shown) is returned to a return electrode connection of the generator 1102 through the monitor 1114 in a manner that is similar to prior AEM laparoscopic instruments described, for example, in the Newton '401 patent.

The conductive body 1108 in this embodiment is connected to the reference potential electrode (RPE) 1140 as described above, and the monitor 1114 in the exemplary embodiment includes two separate channels. A first channel 1160 monitors the current flowing from the shield 1120 to the return electrode 1110, and the first channel is configured to alter the power output from the generator 1102 by sending a control signal 1116 to the generator 1102 in the event of a fault condition. In some embodiments, the channel 1160 does not distinguish between a normal and abnormal fault condition, and instead, it simply shuts off the power if a fault condition is detected. A second channel 1170 monitors currents between the conductive body 1108 and the RPE 1140 and alters power imparted to the active electrode 1104 by inhibiting and/or reducing power as described with reference to other embodiments depicted in FIGS. 3-9.

In this embodiment, large currents flowing through an insulation failure of the electrode assembly have a different path than smaller currents flowing through the conductive body 1108, with different monitoring thresholds and monitoring effects. For example, the monitor 1114 may have a fixed current threshold, a fault current threshold proportional to the active current, and/or the monitor 1114 may produce a warning when the threshold is exceeded.

Alternatively, the monitor 1114 may have two thresholds that include a lower threshold that triggers a warning and a higher threshold that triggers a signal 1116 from the monitor 114 to the generator 1102 that reduces power to the active electrode 1104. As previously discussed, fault currents in the conductive body 1108 can be temporarily induced due to tissue or conductive fluid that causes coupling between the active electrode 1104 and the conductive body 1108. Under such a fault condition, a warning rather than an alteration of the power is advantageous. Another advantage of this configuration is that insulation fault currents will have a direct path to the return electrode 1110 and do not challenge the path involving the RPE 1140 and the conductive body 1108.

Figure 12:
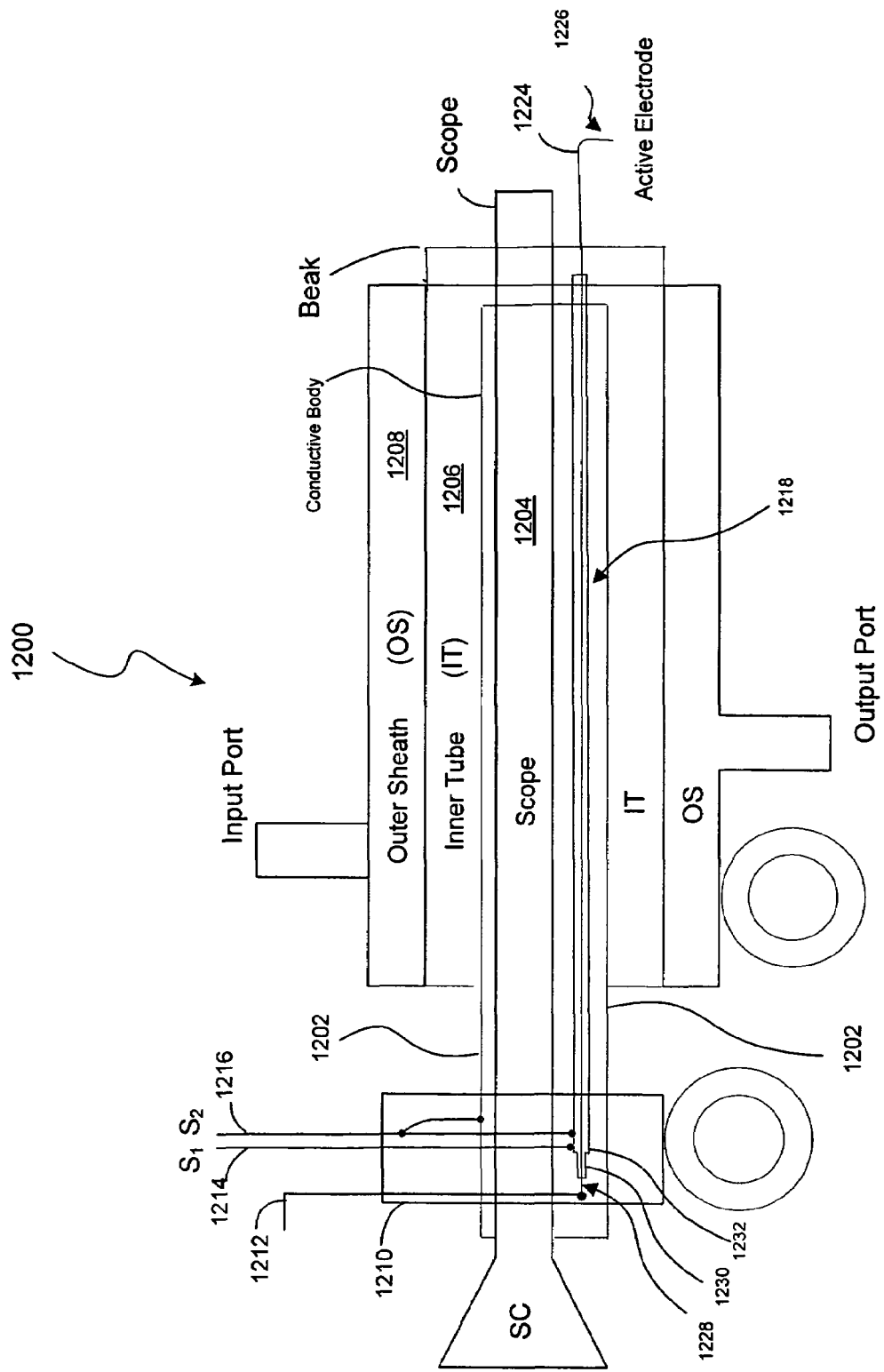
FIG. 12 is a schematic representation of a resectoscope that may be used in connection with the embodiments disclosed with reference to FIGS. 1-9.

Referring next to FIG. 12, shown is a schematic representation of a resectoscope 1200 that may be used in the embodiments disclosed with reference to FIGS. 3-9. As shown, a working element 1202 (i.e., the conductive body of the resectoscope 1200) is coupled to a scope 1204, an inner tube 1206, an outer sheath 1208 and a connector block 1210. As depicted in FIG. 12, the connector block is coupled to an active line 1212, a first shield lead 1214 and a second shield lead 1216.

Also shown is an electrode assembly 1218, which includes an active electrode 1224 with a first end 1226 that is configured to impart a voltage to a region of a patient and a second end 1228 that is configured to detachably couple to the active line 1212 of the connector block 1210. As shown, portions of the active electrode 1224 between the first and second ends 1226, 1228 are surrounded by insulation 1230, and portions of the insulation 1230 are surrounded by a shield 1232, which is detachably coupled to the first and second shield leads 1214, 1216. In several embodiments, a highly conductive material (e.g., gold plating) is employed at the respective interfaces between the shield 1232 and the first and second leads 1214, 1216 and between the active electrode 1224 and the active line 1212. The insulation 1230 in the exemplary embodiment may be composed of a variety of plastics including polyaryletheretherketone (e.g., sold under the PEEK™ brand) and fiber reinforced polymer. The shield 1232 in this embodiment is a conductive material that may include stainless steel and/or aluminum.

In this configuration, the connector block 1210 is added to the working element 1202 of a standard resectoscopic device in order to provide conductive connections to the working element 1202 and the shield 2332 of the electrode assembly 1218. In the exemplary embodiment, the first and second shield leads 1214, 1216 are both disposed so as to be detachably coupled with different portions of the shield 1232. The two shield leads 1214, 1216 provide a redundant, and hence more reliable, coupling to the shield 1232. In addition, the two leads 1214, 1216 enable the connection between the shield leads 1214, 1216 and the shield 1232 to be tested by measuring the continuity between the shield leads 1214, 1216. In this way, when the active electrode assembly 1218 is inserted into the resectoscope 1200, a simple continuity test ensures the electrode assembly is properly engaged with the resectoscope 1200.

As depicted in FIG. 12, the second shield lead 1216 in this embodiment is coupled to the working element 1202 so as to conductively couple the shield 1232 and the working element 1202. In this way, both the shield 1232 and the working element 1302 may be conveniently coupled to a reference potential (e.g., the reference potential 420) via a monitor (e.g., the monitor 114, 214, 314, 414, 614, 714 and 1014).

In this embodiment, the inner tube 1206 and outer sheath 1208 are also coupled to the working element 1202 so that the working element 1202, the shield 1232, the inner tube 1206 and the outer tube 1208 have substantially the same voltage. Both the inner tube 1206 and outer sheath 1208 have a low resistance conduction to the working element 1202. A gold plating, or other good conductor, are preferential solutions for this purpose.

The connector block 1210 also provides a connection between the active electrode 1224 and the active electrode lead 1212. In this embodiment, the working element 1202, scope 1204 and inner tube 1206 are metallic. The outer sheath 1208, however, is metallic in some variations and is an insulator (e.g., fiber reinforced plastic) in other variations.

In some variations of the embodiment depicted in FIG. 12, the second shield lead 1216 is disconnected from the working element 1202 and a separate lead to the working element 1202 is provided within the connector block so as to enable both the shield 1232 and the working element 1202 to be coupled to the separate channels of the dual channel monitor 1114 described with reference to FIG. 11. In yet other variations, the electrode assembly 1000 described with reference to FIG. 10 may be employed in the resectoscope depicted in FIG. 12.

Figure 13B:
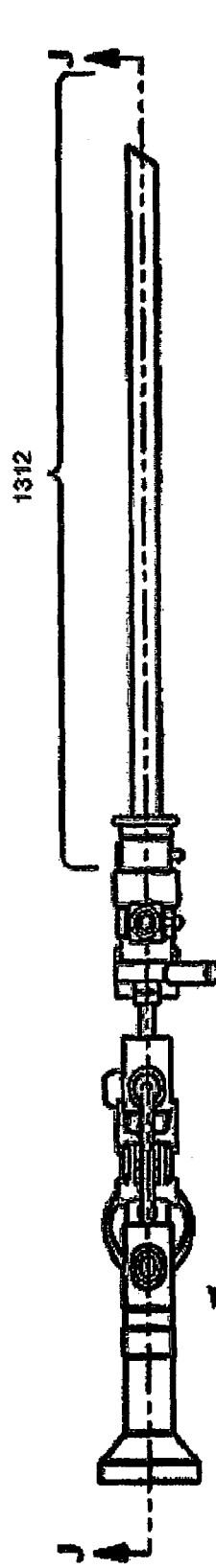
FIGS. 13A, 13B and 13C depict respective front, top and cross sectional views of an exemplary embodiment of a resectoscope that may be used in the embodiments disclosed with reference to FIGS. 1-11.
Figure 13C:
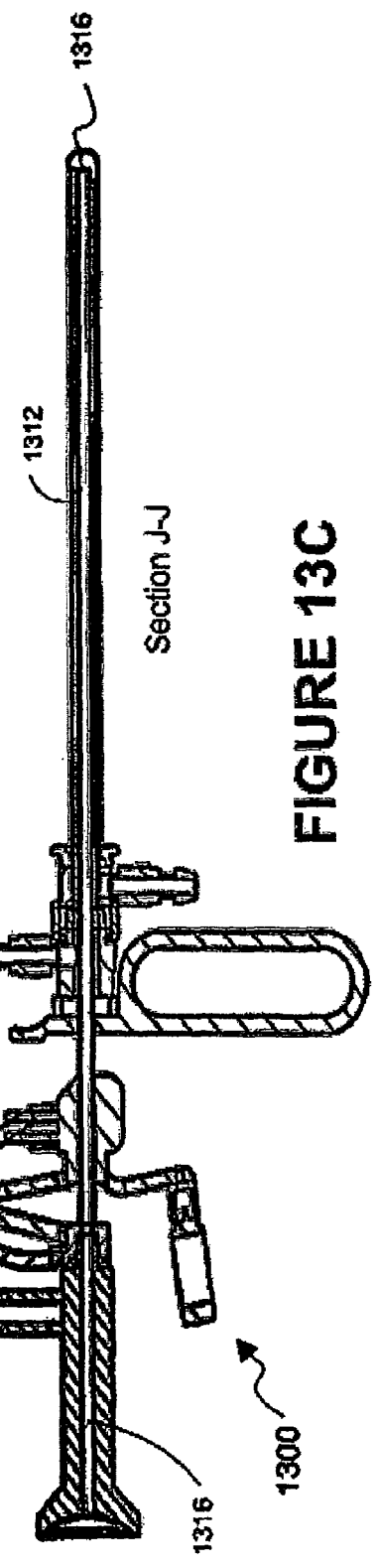
Figure 13A:
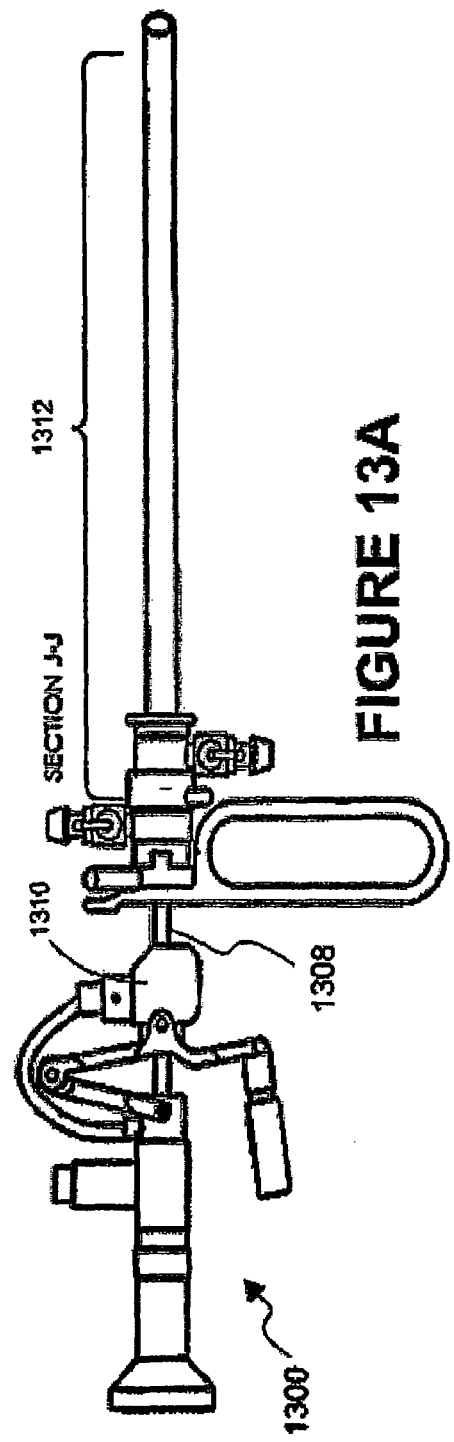

Referring next to FIGS. 13A, 13B and 13C, shown are a front, a top and a cross sectional view of an exemplary embodiment of a resectoscope 1300. As shown in FIGS. 13A and 13B, a working element 1308 is coupled to a connector block 1310 and an outer tube assembly 1312. In FIG. 13C, which is a cross-sectional view of the resectoscope 1300 taken along section J-J of FIG. 13B, shown is a telescope portion 1316 of the resectoscope 1300 within the working element 1308 and the outer tube assembly 1312.

Figure 14:
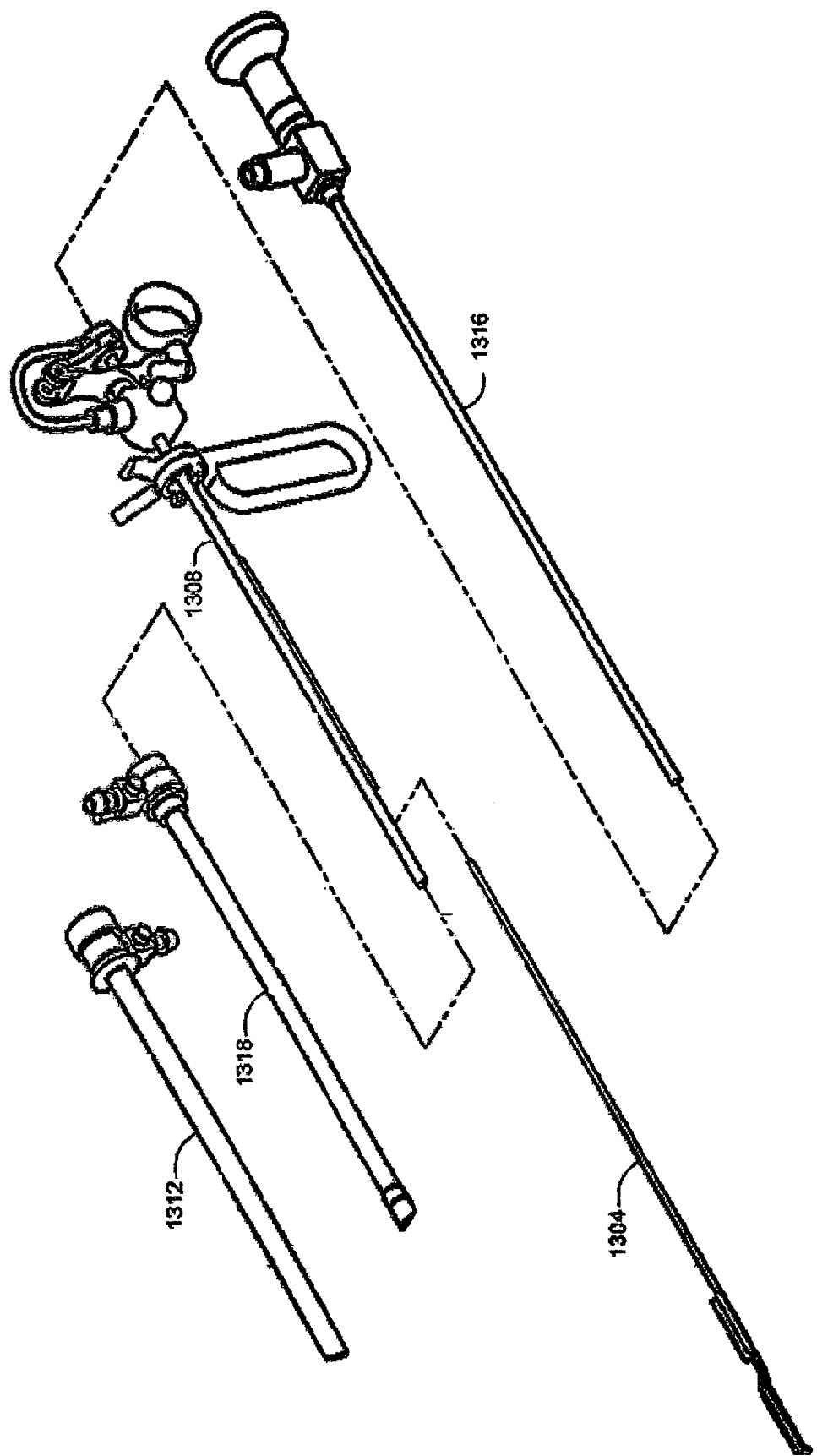
FIG. 14 a perspective view of the resectoscope depicted in FIG. 13 in a disassembled form.

Referring to FIG. 14, shown is a perspective view of the resectoscope depicted in FIG. 13 in a disassembled form. As shown, the telescope assembly 1316 is configured to fit within the working element 1308, and the electrode assembly 1304 is configured to couple to an exterior portion of the working element 1308 so as to be able to move relative to the working element 1308. Also shown is an inner tube assembly 1318 that is configured to slide over both the electrode assembly 1304 and the working element 1308. In addition, the outer tube assembly 1312 is configured to slide over the inner tube assembly 1318.

Figure 15A:
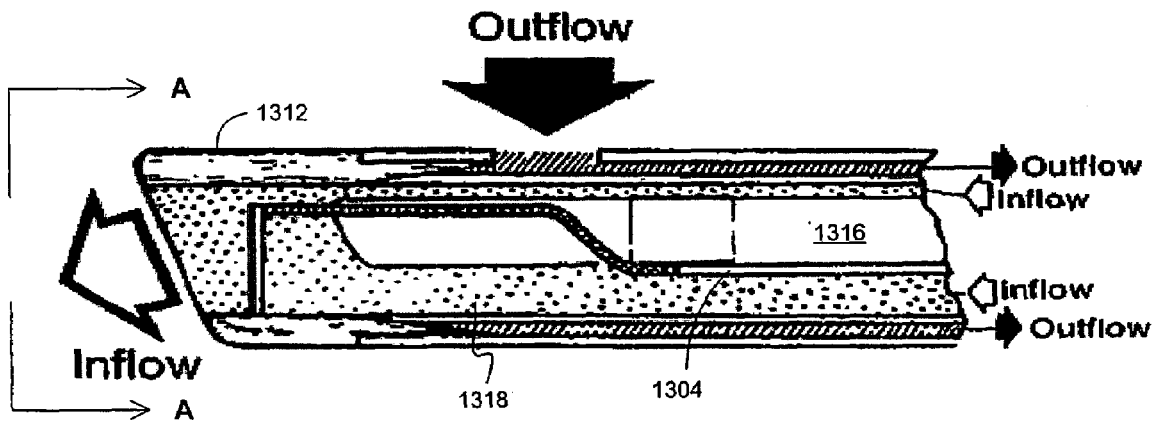
FIGS. 15A and 15B are a cross sectional and a front views of a portion of the resectoscope depicted in FIGS. 13 and 14.
Figure 15B:
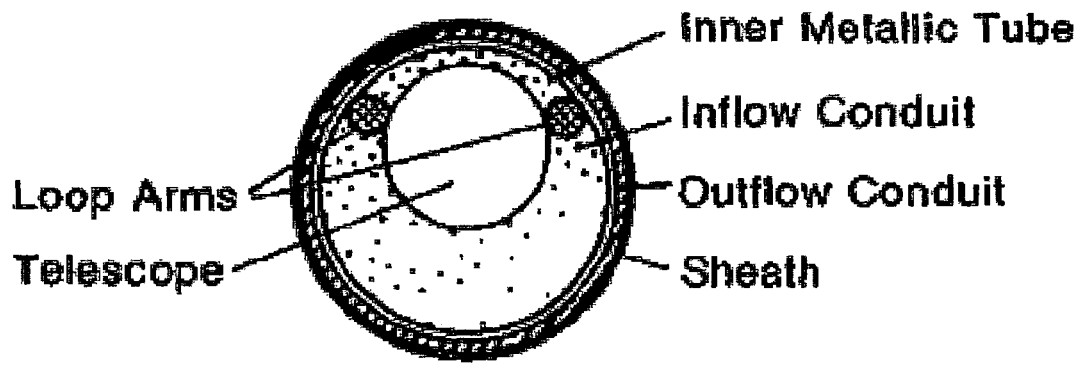

Referring next to FIGS. 15A and 15B, shown are a cross sectional and a front view of a portion of the resectoscope depicted in FIGS. 13 and 14. As shown in FIGS. 15A and 15B, the telescope 1316 and active electrode assembly 1304 fit within the inner tube assembly 1318 while providing sufficient space for the inflow of irrigating fluid.

In conclusion, the present invention provides, among other things, a system and method for monitoring, and rendering safer, electrosurgical procedures. Those skilled in the art can readily recognize that numerous variations and substitutions may be made in the invention, its use and its configuration to achieve substantially the same results as achieved by the embodiments described herein. For example, many of the embodiments described herein are generally applicable to a range of electrosurgical procedures and devices. Accordingly, there is no intention to limit the invention to the disclosed exemplary forms. Many variations, modifications and alternative constructions fall within the scope and spirit of the disclosed invention as expressed in the claims.

What is claimed is:

1. An electrosurgical apparatus comprising:
  a tubular and elongate conductive body including a proximal end and a distal end, the conductive body being configured to surround a scope such that an eye piece of the scope, when coupled to the conductive body, extends axially from the proximal end of the conductive body, and wherein the conductive body is configured to surround a removable active electrode assembly such that an active electrode of the active electrode assembly extends axially from the distal end of the conductive body;
  a connector block coupled to the proximal end of the conductive body, the connector block extending radially from the conductive body and being configured to detachably couple with the active electrode assembly, wherein the connector block includes:
    a conductive lead coupled to the conductive body, the conductive lead being electrically isolated from the active electrode so as to enable fault current between the conductive body and the active electrode to be monitored;
    a shield contact disposed so as to be capable of detachably and electrically coupling with a conductive shield of the active electrode assembly, wherein the shield contact is coupled to a shield lead, wherein the shield lead is disposed so as to be capable of coupling with a monitor; and
  an active electrode contact disposed so as to be capable of detachably coupling with the active electrode of the active electrode assembly;
  wherein the conductive body is positioned relative to the connector block such that when an active electrode assembly is coupled to the connector block, the conductive body is electrically insulated from an active electrode of the active electrode assembly, but a temporary, yet tolerable, conduction, via conductive fluids interposed between the active electrode and the conductive body, may occur between the conductive body and the active electrode during an electrosurgical procedure.

2. The electrosurgical apparatus of claim 1 including: an insulating sheath surrounding at least a portion of the conductive body so as to insulate a patient from components of the electrosurgical apparatus when a tip of the active electrode is imparting a voltage to the patient.

3. The electrosurgical apparatus of claim 1, wherein the shield contact is conductively coupled to the conductive body so as to be capable of rendering the conductive shield of the active electrode assembly the same voltage as a voltage of the conductive body.

4. The electrosurgical apparatus of claim 3, wherein the shield contact is conductively coupled to the conductive body via the conductive lead.

5. The electrosurgical apparatus of claim 1, wherein the shield contact is electrically isolated from the conductive body.

6. The electrosurgical apparatus of claim 1, wherein the connector block includes a second shield contact disposed so as to be capable of detachably coupling with the conductive shield of the active electrode assembly.

7. A method of adapting an electrosurgical apparatus comprising:
providing a connector block configured to detachably couple with an active electrode assembly;
providing a shield contact to couple to the connector block, the shield contact disposed so as to be capable of detachably and electrically coupling with a conductive shield of the active electrode assembly;
providing a conductive lead coupled to the conductive body, the conductive lead being electrically isolated from the active electrode so as to enable fault current between the conductive body and the active electrode to be monitored;
providing an active electrode contact to couple to the connector block, the active electrode contact disposed so as to be capable of detachably coupling with an active electrode of the active electrode assembly; and
providing a tubular and elongate conductive body, the conductive body including a proximal end and a distal end, wherein the proximal end of the conductive body is configured to couple with the connector block, and the conductive body is configured to surround a scope such that an eye piece of the scope, when coupled to the conductive body, extends axially from the proximal end of the conductive body, and wherein the conductive body is configured to surround the active electrode assembly such that an active electrode of the active electrode assembly is electrically isolated from the active electrode and extends axially from the distal end of the conductive body, but a temporary, yet tolerable, conduction, via conductive fluids interposed between the active electrode and the conductive body, may occur during an electrosurgical procedure.

8. The method of claim 7 including:
providing an insulating sheath configured to surround at least a portion of the conductive body so as to insulate a patient from components of the electrosurgical apparatus when a tip of the active electrode is imparting a voltage to the patient.

9. The method of claim 7, wherein providing the shield contact includes providing a shield contact that is configured to conductively couple to the conductive body so as to be capable of rendering the conductive shield of the active electrode assembly the same voltage as a voltage of the conductive body.

10. The electrosurgical apparatus of claim 9, wherein the shield contact is conductively coupled to the conductive body via the conductive lead.

11. The method of claim 7, wherein providing the shield contact includes providing a shield contact that is configured to be electrically isolated from the conductive body.

12. An electrosurgical apparatus comprising:
a tubular and elongate working element including a proximal end and a distal end;
a connector block coupled to the proximal end of the working element, the connector block extending radially from the working element, wherein the connector block includes:
a conductive lead coupled to the working element, the conductive lead being electrically isolated from the active electrode and disposed so as to enable the working element to be conductively coupled with a monitor;
a shield contact coupled to a shield lead, the shield lead is disposed so as to be capable of coupling with the monitor; and
an active electrode contact coupled to an active electrode lead, the active electrode lead disposed so as to be capable of coupling with a power generator;
an active electrode assembly detachably coupled to the connector block, the active electrode assembly including:
an active electrode including a first end detachably coupled to the active electrode contact and a second end configured to impart a voltage to a region of a patient so as to be capable of carrying out an electrosurgical procedure at the region;
a layer of insulation surrounding portions of the active electrode between the first and second ends of the active electrode; and
a conductive shield surrounding portions of the insulation, wherein the shield is configured to detachably and conductively couple to the shield contact of the connector block.

13. The apparatus of claim 12 including a layer of outer insulation surrounding portions of the conductive shield.

14. The electrosurgical apparatus of claim 12, wherein the connector block includes a second shield contact coupled to a second shield lead.

15. The electrosurgical apparatus of claim 12, wherein the shield contact is conductively coupled to the conductive lead so as to be capable of rendering the conductive shield of the active electrode assembly the same voltage as a voltage of the conductive body.

16. The electrosurgical apparatus of claim 12, wherein the shield contact is electrically isolated from the conductive body.

* * * * *